United States Patent
Nagase et al.

(10) Patent No.: US 8,163,898 B2
(45) Date of Patent: Apr. 24, 2012

(54) 4-SULFONYLPIPERIDINE DERIVATIVES

(75) Inventors: Tsuyoshi Nagase, Tokushima (JP); Takahide Sasaki, Kawasaki (JP); Toshiyuki Takahashi, Tsukuba (JP)

(73) Assignee: MSD K. K., Tokyo (JP)

( * ) Notice: Subject to any disclaimer, the term of this patent is extended or adjusted under 35 U.S.C. 154(b) by 207 days.

(21) Appl. No.: 12/674,999

(22) PCT Filed: Sep. 12, 2008

(86) PCT No.: PCT/JP2008/066525
§ 371 (c)(1),
(2), (4) Date: Apr. 2, 2010

(87) PCT Pub. No.: WO2009/038021
PCT Pub. Date: Mar. 26, 2009

(65) Prior Publication Data
US 2010/0234392 A1    Sep. 16, 2010

(30) Foreign Application Priority Data

Sep. 21, 2007 (JP) ................................. 2007-244731

(51) Int. Cl.
C07D 345/00 (2006.01)
C07D 517/00 (2006.01)
C07D 295/00 (2006.01)
C07D 211/60 (2006.01)

(52) U.S. Cl. ........................... 540/1; 544/383; 546/245

(58) Field of Classification Search ...... 540/1; 544/383; 546/245
See application file for complete search history.

(56) References Cited

U.S. PATENT DOCUMENTS
2006/0148739 A1    7/2006 Kotani et al.
2010/0056597 A1    3/2010 Takahashi et al.

FOREIGN PATENT DOCUMENTS
| DE | 197 43 435 A1 | 10/1997 |
| EP | 1 657 311 A1 | 5/2006 |
| EP | 2 058 305 A1 | 5/2009 |
| WO | 97/21707 A1 | 6/1997 |
| WO | 97/28141 A1 | 8/1997 |
| WO | 2009/044788 A1 | 4/2009 |
| WO | 2009/081789 A1 | 7/2009 |
| WO | 2009/099086 A1 | 8/2009 |
| WO | 2009/131065 A1 | 10/2009 |

OTHER PUBLICATIONS

Lee, S.H. et al., "Fatty Acid Synthesis by Elongases in Trypanosomes", Cell, 2006, pp. 691-699, vol. 126.
Matsuzaka, T. et al., "Cloning and characterization of a mammalian fatty acyl-CoA elongase as a lipogenic enzyme regulated by SREBPs", Journal of Lipid Research, 2002, pp. 911-920, vol. 43.

*Primary Examiner* — Marcos Sznaidman
(74) *Attorney, Agent, or Firm* — Janet E. Fair; John C. Todaro

(57) ABSTRACT

[PROBLEMS]
To provide compounds useful as preventives or remedies for circulatory diseases, nervous diseases, metabolic diseases, reproductive system diseases, and digestive diseases.
[MEANS FOR SOLVING PROBLEMS]
Compounds represented by the general formula (I) or pharmaceutically acceptable salts thereof:

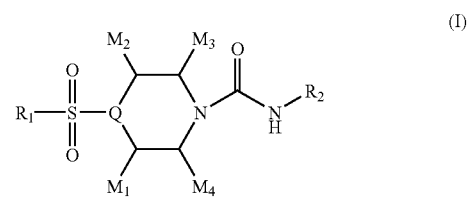

wherein R1 is C1-6 alkyl, C3-8 cycloalkyl, or the like; R2 is phenyl, heteroaryl, or the like; Q is N or CH; and M1, M2, M3 and M4 are each independently hydrogen or C1-6 alkyl, or alternatively M1 together with M2 or M3 forms —CH2-CH2- or the like, or M4 together with M2 or M3 forms —CH2-CH2- or the like, with the proviso that M1, M2, M3, and M4 are such that one —CH2- or —CH2-CH2- group is formed thereamong.

11 Claims, No Drawings

4-SULFONYLPIPERIDINE DERIVATIVES

CROSS-REFERENCE TO RELATED APPLICATIONS

This application is a U.S. National Phase application under 35 U.S.C. §371 of PCT Application No. PCT/JP2008/066525, filed Sep. 12, 2008, which published as WO 2009/038021 A1 on Mar. 26, 2009, and claims priority under 35 U.S.C. §365(b) from Japanese patent application No. JP2007-244731, filed Sep. 21, 2007.

TECHNICAL FIELD

The present invention is useful in the medical field. More specifically, the 4-sulfonylpiperidine derivative of the invention is useful as a long chain fatty acyl elongase (hereinafter sometimes referred to as LCE) inhibitor for use as a remedy for various kinds of circulatory diseases, neurological diseases, metabolic diseases, reproductive system diseases, digestive diseases, neoplasms, infectious diseases, and the like, or as a herbicide.

BACKGROUND ART

Obesity is a condition where the energy intake is continuously excessive relative to the energy consumption, thereby causing accumulation of neutral fat in fat cells, resulting in remarkably increased body weight over the standard body weight (Eiji Itagaki, STEP Taisha/Naibunpitsu (STEP metabolism/endocrine), Kaibashobo, 1$^{st}$. Ed., p. 105, 1998). It is known that excessive accumulation of fat causes, for example, insulin resistance, diabetes, hypertension, hyperlipidemia, and the like, and that combination a plurality of these factors greatly increases the risk of the onset of atherosclerosis. Such a condition is called metabolic syndrome. Further, hypertriglyceridemia and obesity are known to increase the risk of pneumonia, hepatic dysfunction, cancers such as breast cancer, uterine cancer, ovarian cancer, colon cancer, and prostatic cancer, emmeniopathy, arthritis, gout, cholecystitis, gastroesophageal reflux, obesity hypoventilation syndrome (Pickwickian syndrome), sleep apnea syndrome, and the like. It is widely known that diabetes often leads to, onset of, for example, angina pectoris, cardiac insufficiency, stroke, claudication, retinopathy, visual loss, renal insufficiency, neuropathy, skin ulcer, infection, and the like [The Merck Manual of Medical Information, 2$^{nd}$ Home Edition, Merck & Co, 2003].

LCE is an enzyme that exists in the endoplasmic reticulum in cells. In the group of enzymes that catalyze the carbon-chain elongation reaction of fatty acids of chain length $C_{12}$ or longer, LCE is an enzyme that catalyzes the rate-limiting condensation step. In the mammals, most of fatty acids newly synthesized in vivo have a chain length of $C_{16}$ to $C_{18}$. Such long chain fatty acids account for more than 90% of the total fatty acids existing in cells. They are important constituents of the membrane, and are also the basic components of the fatty tissue, the greatest energy conservation organ in animals. Synthesis of new fatty acids most likely takes place in the liver, and such synthesis converts excessive glucose in the body into fatty acids. Glucose is converted by glycolysis into pyruvate. Pyruvate is converted in the mitochondria into citrate, and conveyed to the cytosol. ATP citrate lyase in the cytosol produces fatty acids and acetyl-CoA, a precursor of cholesterol. Acetyl-CoA is carboxylated by acetyl-CoA carboxylase (ACC) to form malonyl-CoA. Fatty acid synthase (FAS), a multifunctional enzyme, elongates fatty acids by 2 carbons, using malonyl-CoA, acetyl-CoA, and NADPH. The main final product of FAS in the rodents is palmitoyl-CoA having a chain length of $C_{16}$, and LCE elongates the carbon chain of such palmitoyl-CoA by further 2 carbons [J. Biol. Chem., 276 (48), 45358-45366, (2001)]. Excessive acceleration of fatty acid synthesis in vivo is known to cause an increase in neutral fat and the like, which thus is responsible for the accumulation of fats. For example, WO 2005/005665 (Patent Document 1) shows a direct relation between LCE and obesity. Moreover, changes in the mouse FACE (LCE) expression level due to food intake have also been reported (Matsuzaka T. et al., J, Lipid Res., 43(6): 911-920 (2002); Nonpatent Document 1).

LCE is known to exist also in protozoa and nematodes, and be involved in cell proliferation. For example, it has been disclosed that in trypanosomatid protozoa that cause the African trypanosomiasis (vernacular name: African sleeping sickness), long chain fatty acids are synthesized via the fatty acid elongation pathway involving LCE, and that inhibition of intracellular fatty acid elongation reaction affects the proliferation of trypanosomatid protozoa (Lee S. H. et al., Cell, 126: 691-699 (2006); Nonpatent Document 2).

No compound has been known to have LCE inhibitory effect. Meanwhile, the compound of the invention is a piperidine derivative having a sulfonyl group at the 4-position of piperidine (or piperazine), while no compound has been known with the piperidine (or piperazine) moiety forming a bicyclo ring, wherein an aryl group or the like is bound to the nitrogen atom of the piperidine (or piperazine) through a linker.

Patent Document 1: WO 2005/005665 pamphlet
Nonpatent Document 1: J. Lipid Res., 43 (6), pp. 911-920 (2002)
Nonpatent Document 2: Cell, 126: pp. 691-699 (2006)

DISCLOSURE OF THE INVENTION

Problems that the Invention is to Solve

The object of the invention is to provide a novel compound having LCE inhibitory effect.

Means for Solving the Problems

As a result of extensive research, the present inventors found that a specific piperidine (or piperazine) derivative having a sulfonyl group at the 4-position of the piperidine (or piperazine) skeleton has excellent LCE inhibitory effect, and thus accomplished the invention.

Specifically, the invention provides:
(1) a compound represented by formula (I) or a pharmaceutically acceptable salt thereof (hereinafter referred to as a "compound of the invention"):

[Chemical Formula 1]

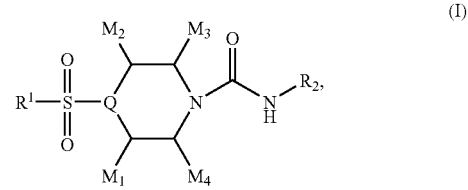

wherein:

R$^1$ represents optionally substituted C$_{1-6}$ alkyl, optionally substituted C$_{3-8}$ cycloalkyl, optionally substituted aryl, or optionally substituted heteroaryl, wherein the C$_{1-6}$ alkyl, C$_{3-8}$ cycloalkyl, aryl, or heteroaryl optionally having a substituent selected from the group consisting of halogen, C$_{1-6}$ alkyl, halo C$_{1-6}$ alkyl, C$_{1-6}$ alkyloxy, and halo C$_{1-6}$ alkyloxy;

R$^2$ represents optionally substituted phenyl or optionally substituted heteroaryl, wherein the phenyl or heteroaryl optionally having a substituent selected from the group consisting of halogen, C$_{1-6}$ alkyl, halo C$_{1-6}$ alkyl, C$_{3-8}$ cycloalkyl, C$_{1-6}$ alkyloxy, phenyl, and nitrogen-containing heteroaryl;

Q represents N or CH;

M$_1$ and M$_2$ each independently represent a hydrogen atom or C$_{1-6}$ alkyl optionally substituted with halogen, or M$_1$ forms, together with M$_2$ or M$_3$, —CH$_2$— or —CH$_2$—CH$_2$—; and M$_3$ and M$_4$ each independently represent a hydrogen atom or C$_{1-6}$ alkyl optionally substituted with halogen, or M$_4$ forms, together with M$_2$ or M$_3$, —CH$_2$— or —CH$_2$—CH$_2$—, provided that M$_1$, M$_2$, M$_3$, and M$_4$ provide one —CH$_2$— or —CH$_2$—CH$_2$—.

Further, the invention also provides:

(2) a long chain fatty acyl elongase (LCE) inhibitor comprising as an active ingredient a compound represented by formula (I) or a pharmaceutically acceptable salt thereof, (3) a pharmaceutical composition comprising a compound represented by formula (I) or a pharmaceutically acceptable salt thereof, and (4) a preventive or a remedy for diabetes, obesity, or non-alcoholic fatty liver disease, comprising as an active ingredient a compound represented by formula (I) or a pharmaceutically acceptable salt thereof.

Further, because of its LCE inhibitory effect, the compound of the invention is useful as a preventive or a remedy for various LCE-associated diseases, including hypertension, angina pectoris, cardiac insufficiency, myocardial infarction, stroke, claudication, diabetic nephropathy, diabetic retinopathy, visual loss, electrolyte abnormality, atherosclerosis, and like circulatory diseases; bulimia, diabetic neuropathy, and like central neurological diseases; metabolic syndrome, obesity, diabetes, insulin resistance, hyperlipidemia, hypercholesterolemia, hypertriglyceridemia, dyslipidemia, non-alcoholic fatty liver disease, inappropriate hormone secretion, gout, fatty liver, and like metabolic diseases; menstrual disorder, sexual dysfunction, and like reproductive system diseases; hepatic dysfunction, pancreatitis, cholecystitis, gastroesophageal reflux, and like digestive diseases; obesity hypoventilation syndrome (Pickwickian syndrome), sleep apnea syndrome, and like respiratory diseases; infectious diseases caused by bacteria, fungi, and parasites; neoplasm; arthritis, skin ulcer, and like inflammatory diseases; and the like, or as a herbicide.

In particular, the compound of the invention is useful as a remedy for, for example, diabetes, obesity, non-alcoholic fatty liver disease, or the like, or as a herbicide.

Hereinafter, the terms used herein will be descried to explain the compound of the invention in further detail.

The term "halogen atom" means a fluorine atom, a chlorine atom, a bromine atom, or an iodine atom.

The term "C$_{1-6}$ alkyl" means a straight or branched alkyl group having a carbon number of 1 to 6, examples thereof including methyl, ethyl, propyl, isopropyl, butyl, isobutyl, sec-butyl, tert-butyl, pentyl, isopentyl, hexyl, isohexyl, and the like.

The term "halo C$_{1-6}$ alkyl" means a C$_{1-6}$ alkyl group as above substituted at an arbitrary substitutable position(s) with one or more, preferably one to three, same or different halogen atoms as above, examples thereof including fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl, and the like.

The term "C$_{3-8}$ cycloalkyl" means cycloalkyl having a carbon number of 3 to 8, examples thereof including cyclopropyl, cyclobutyl, cyclopentyl, cyclohexyl, and the like.

The term "C$_{1-6}$ alkyloxy" means a straight or branched alkyloxy group having a carbon number of 1 to 6, examples thereof including methoxy, ethoxy, propoxy, isopropoxy, butoxy, sec-butoxy, isobutoxy, tert-butoxy, pentyloxy, isopentyloxy, hexyloxy, isohexyloxy, and the like.

The term "halo C$_{1-6}$ alkyloxy" means a C$_{1-6}$ alkyloxy group as above substituted at an arbitrary substitutable position(s) with one or more, preferably one to three, same or different halogen atoms as above, examples thereof including fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy, and the like.

"Aryl" is, for example, phenyl, naphthyl, or the like.

The term "heteroaryl" means 5- or 6-membered monocyclic heteroaryl containing one or more, preferably one to three, same or different heteroatoms selected from the group consisting of an oxygen atom, a nitrogen atom, and a sulfur atom, or otherwise means condensed-ring heteroaryl formed by condensation of such monocyclic heteroaryl and the above-mentioned aryl or alternatively by mutual condensation of the same or different monocyclic heteroaryl groups. Examples thereof include pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyldinyl, 1,3,5-triazinyl, indolyl, benzofuranyl, benzothienyl, benzimidazolyl, benzopyrazolyl, benzoxazolyl, benzisoxazolyl, benzothiazolyl, benzisothiazolyl, indazolyl, purinyl, quinolyl, isoquinolyl, phthalazinyl, naphthyridinyl, quinoxalinyl, quinazolinyl, cinnolinyl, pteridinyl, pyrido[3,2-b]pyridyl, and the like.

A "salt" of the compound of the invention means an ordinary, pharmaceutically acceptable salt. Examples thereof include salts such as, in the case where a carboxyl group is contained, base addition salts of the carboxyl group and, in the case where an amino group or a basic heterocyclic group is contained, acid addition salts in the basic heterocyclic group.

Examples of the base addition salt include alkali metal salts such as sodium salts, and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts, and so on.

Examples of the acid addition salt include inorganic acid salts such as hydrochlorides, sulfates, nitrates, phosphates, perchlorates and so on; organic acid salts such as maleates, fumarates, tartrates, citrates, ascorbates, trifluoroacetates and so on; and sulfonates such as methanesulfonates, isethionates, benzenesulfonates, p-toluenesulfonates and so on.

For more specific disclosure of the compound of the invention, the symbols used in formula (I) will be explained through preferred specific examples.

The term "arbitrary substitutable position" indicates a position having a chemically substitutable hydrogen atom on a carbon atom, a nitrogen atom, an oxygen atom, and/or a sulfur atom, and which provides a chemically stable compound as a result of the substitution.

Depending on the type of substituent therein or the salt type, the compound of the invention may exist as a stereoisomer or a tautomer, such as an optical isomer, a diastereomeric isomer, or a geometrical isomer. The compound of the invention also includes all such stereoisomers, tautomers, and mixtures thereof.

The invention includes various crystals, amorphous substances, salts, hydrates, and solvates of the compound of the invention.

Further, a prodrug of the compound of the invention is also within the scope of the invention. In general, such a prodrug is a functional derivative of the compound of the invention, which can be readily converted into a required compound in vivo. Accordingly, in the method of the invention for the treatment of various diseases, the term "administration" includes not only the administration of a specified compound but also the administration of a compound that is converted, after administration to a patient, into the specified compound in vivo. The usual practice for selection and production of a suitable prodrug derivative is described, for example, in "Design of Prodrugs", ed. H. Bundgaard, Elsevier, 1985, etc., and its entire description is referred to and incorporated herein as a part of the specification of the present application. Metabolites of these compounds include active compounds that are produced by placing compounds of the invention in a biological environment, and they are within a scope of the invention.

Hereinafter, for specific disclosure of the compound of the invention, the symbols used in formula (I) will be explained with reference to specific examples.

$R^1$ represents optionally substituted $C_{1-6}$ alkyl, optionally substituted $C_{3-8}$ cycloalkyl, optionally substituted aryl, or optionally substituted heteroaryl, and wherein the $C_{1-6}$ alkyl, $C_{3-8}$ cycloalkyl, aryl, or heteroaryl optionally has a substituent selected from the group consisting of halogen, $C_{1-6}$ alkyl, halo $C_{1-6}$ alkyl, $C_{1-6}$ alkyloxy, and halo $C_{1-6}$ alkyloxy.

With respect to $R^1$, $C_{1-6}$ alkyl may be methyl, ethyl, n-propyl, isopropyl, n-butyl, or the like, for example; $C_{3-8}$ cycloalkyl may be cyclopropyl, cyclobutyl, cyclopentyl, cyclohexyl, or the like, for example; aryl may be phenyl, naphthyl, or the like, for example; and heteroaryl may be pyrazolyl, pyridyl, pyrimidinyl, pyridazinyl, pyrazinyl, triazolyl, tetrazolyl, thiazolyl, thiadiazolyl, imidazolyl, isothiazolyl, oxazolyl, isoxazolyl, oxadiazolyl, 1,2,4-triazinyl, 1,3,5-triazinyl, or the like, for example.

The $C_{1-6}$ alkyl, $C_{3-8}$ cycloalkyl, aryl, or heteroaryl may have a substituent selected from the group consisting of halogen, $C_{1-6}$ alkyl, halo $C_{1-6}$ alkyl, $C_{1-6}$ alkyloxy, and halo $C_{1-6}$ alkyloxy.

Examples of such substituents include fluorine, chlorine, bromine, or like halogen; methyl, ethyl, n-propyl, isopropyl, n-butyl, or like $C_{1-6}$ alkyl; chloromethyl, fluoromethyl, trifluoromethyl, chloroethyl, fluoroethyl, difluoroethyl, or like halo $C_{1-6}$ alkyl; methoxy, ethoxy, n-propyloxy, isopropyloxy, or like $C_{1-6}$ alkyloxy; and chloromethoxy, fluoromethoxy, trifluoromethoxy, or like $C_{1-6}$ alkyloxy.

Specifically, $R^1$ may be phenyl, 4-fluorophenyl, 2-methoxypheny, 3-methoxypheny, 4-methoxypheny, 2-chlorophenyl, 3-chlorophenyl, 4-chlorophenyl, 2-pyrimidinyl, 2-pyridinyl, 3-pyridinyl, 4-pyridinyl, 1,2,4-triazol-3-yl, thiazol-2-yl, or the like, for example. Preferably, phenyl, 4-fluorophenyl, pyridin-2-yl, and pyrimidin-2-yl are recommended.

$R^2$ represents optionally substituted phenyl or optionally substituted heteroaryl, and wherein the phenyl or heteroaryl may have a substituent selected from the group consisting of halogen, $C_{1-6}$ alkyl, halo $C_{1-6}$ alkyl, $C_{3-8}$ cycloalkyl, $C_{1-6}$ alkyloxy, phenyl, and nitrogen-containing heteroaryl.

Preferred examples of heteroaryl include pyridyl, pyrazolyl, thiadiazolyl, and the like.

Specific examples of substituents that optionally substitute for phenyl or heteroaryl include fluorine, chlorine, bromine, or like halogen; methyl, ethyl, n-propyl, isopropyl, n-butyl, tert-butyl, or like $C_{1-6}$ alkyl; chloromethyl, fluoromethyl, trifluoromethyl, chloroethyl, fluoroethyl, difluoroethyl, or like halo $C_{1-6}$ alkyl; cyclopropyl, cyclobutyl, cyclopentyl, cyclohexyl, or like $C_{3-8}$ cycloalkyl; methoxy, ethoxy, n-propyloxy, isopropyloxy, or like $C_{1-6}$ alkyloxy; phenyl; and pyrazolyl, pyridinyl, pyrazinyl, pyrimidinyl, or like nitrogen-containing heteroaryl.

Specifically, $R^2$ may be phenyl, 4-methylphenyl, 4-isopropylphenyl, 4-tert-butylphenyl, 4-fluorophenyl, 4-chlorophenyl, 4-trifluoromethylphenyl, 3-trifluoromethylphenyl, 2-trifluoromethylphenyl, 2-pyridinyl, 3-pyridinyl, 4-pyridinyl, 3,5-bis(trifluoromethyl)phenyl, 4-cyclohexylphenyl, 2-methoxypheny, 3-methoxypheny, 4-methoxypheny, 4-isopropyloxyphenyl, 4-biphenyl, 4-(1H-pyrazol-3-yl)-phenyl, 4-(1,3,4-thiadiazol-2-yl)-phenyl, 6-trifluoromethylpyridin-3-yl, 5-trifluoromethylpyridin-2-yl, or the like.

Preferably, $R^2$ is optionally substituted phenyl or optionally substituted pyridinyl. More preferably, (4-trifluoromethyl)phenyl, 4-isopropylphenyl, 5-(trifluoromethyl)pyridin-3-yl, 5-(trifluoromethyl)pyridin-2-yl, and 4-tert-butylphenyl are recommended.

Q represents N or CH.

Q is preferably CH.

$M_1$ and $M_2$ each independently represent a hydrogen atom or $C_{1-6}$ alkyl optionally substituted with halogen, or $M_1$ forms, together with $M_2$ or $M_3$, —$CH_2$— or —$CH_2$—$CH_2$—.

Specifically, $M_1$ and $M_2$ may each be a hydrogen atom, methyl, ethyl, n-propyl, an n-butyl group, chloromethyl, fluoromethyl, trifluoromethyl, or the like. Further, $M_1$ and $M_2$ may together form —$CH_2$— or —$CH_2$—$CH_2$—, or $M_1$ and $M_3$ may together form —$CH_2$— or —$CH_2$—$CH_2$—.

$M_3$ and $M_4$ each independently represent a hydrogen atom or $C_{1-6}$ alkyl optionally substituted with halogen, or $M_4$ forms, together with $M_2$ or $M_3$, —$CH_2$— or —$CH_2$—$CH_2$—.

Specifically, $M_3$ and $M_4$ may each be a hydrogen atom, methyl, ethyl, n-propyl, n-butyl, chloromethyl, fluoromethyl, trifluoromethyl, or the like. Further, $M_4$ and $M_2$ may together form —$CH_2$— or —$CH_2$—$CH_2$—, or $M_4$ and $M_3$ may together form —$CH_2$— or —$CH_2$—$CH_2$—.

However, $M_1$, $M_2$, $M_3$, and $M_4$ form one —$CH_2$— or —$CH_2$—$CH_2$—.

Specific examples of combinations of $M_1$, $M_2$, $M_3$, and $M_4$ include:

1) $M_1$ forms, together with $M_2$, —$CH_2$— or —$CH_2$—$CH_2$—, and $M_3$ and $M_4$ are each independently a hydrogen atom or $C_{1-6}$ alkyl optionally substituted with halogen, 2) $M_1$ forms, together with $M_3$, —$CH_2$— or —$CH_2$—$CH_2$—, and $M_2$ and $M_4$ are each independently a hydrogen atom or $C_{1-6}$ alkyl optionally substituted with halogen, 3) $M_4$ forms, together with $M_3$, —$CH_2$— or —$CH_2$—$CH_2$—, and $M_1$ and $M_2$ are each independently a hydrogen atom or $C_{1-6}$ alkyl optionally substituted with halogen, and 4) $M_4$ forms, together with $M_2$, —$CH_2$— or —$CH_2$—$CH_2$—, and $M_1$ and $M_3$ are each independently a hydrogen atom or $C_{1-6}$ alkyl optionally substituted with halogen.

Preferred combinations of $M_1$, $M_2$, $M_3$, and $M_4$ are:

1) $M_1$ forms, together with $M_2$, —$CH_2$— or —$CH_2$—$CH_2$—, and $M_3$ and $M_4$ are each independently a hydrogen atom or $C_{1-6}$ alkyl optionally substituted with halogen, and 2) M$_4$ forms, together with M$_3$, —CH$_2$— or —CH$_2$—CH$_2$—, and M$_1$ and M$_2$ are each independently a hydrogen atom or C$_{1-6}$ alkyl optionally substituted with halogen.

Particularly recommended are:

a) M$_1$ and M$_2$ together form —CH$_2$—CH$_2$—, and M$_3$ and M$_4$ are each a hydrogen atom, and b) M$_4$ and M$_3$ together form —CH$_2$—CH$_2$—, and M$_1$ and M$_2$ are each a hydrogen atom.

Specific examples of compounds represented by formula (I) include:

3-phenylsulfonyl-N-[(4-trifluoromethyl)phenyl]-8-azabicyclo[3.2.1]octane-8-carboxamide,
3-(4-fluorophenyl)sulfonyl-N-[(4-trifluoromethyl)phenyl]-8-azabicyclo[3.2.1]octane-8-carboxamide,
3-[(2-methoxyphenyl)sulfonyl]-N-[(4-trifluoromethyl)phenyl]-8-azabicyclo[3.2.1]octane-8-carboxamide,
3-[(3-methoxyphenyl)sulfonyl]-N-[(4-trifluoromethyl)phenyl]-8-azabicyclo[3.2.1]octane-8-carboxamide,
3-[(4-methoxyphenyl)sulfonyl]-N-[(4-trifluoromethyl)phenyl]-8-azabicyclo[3.2.1]octane-8-carboxamide,
3-[(2-chlorophenyl)sulfonyl]-N-[(4-trifluoromethyl)phenyl]-8-azabicyclo[3.2.1]octane-8-carboxamide,
3-[(3-chlorophenyl)sulfonyl]-N-[(4-trifluoromethyl)phenyl]-8-azabicyclo[3.2.1]octane-8-carboxamide,
3-[(4-chlorophenyl)sulfonyl]-N-[(4-trifluoromethyl)phenyl]-8-azabicyclo[3.2.1]octane-8-carboxamide,
3-(pyridin-2-ylsulfonyl)-N-[(4-trifluoromethyl)phenyl]-8-azabicyclo[3.2.1]octane-8-carboxamide,
3-(pyridin-3-ylsulfonyl)-N-[(4-trifluoromethyl)phenyl]-8-azabicyclo[3.2.1]octane-8-carboxamide,
3-(pyridin-4-ylsulfonyl)-N-[(4-trifluoromethyl)phenyl]-8-azabicyclo[3.2.1]octane-8-carboxamide,
3-(pyrimidin-2-ylsulfonyl)-N-[(4-trifluoromethyl)phenyl]-8-azabicyclo[3.2.1]octane-8-carboxamide,
N-phenyl-3-phenylsulfonyl-8-azabicyclo[3.2.1]octane-8-carboxamide,
N-(4-fluorophenyl)-3-phenylsulfonyl-8-azabicyclo[3.2.1]octane-8-carboxamide,
N-(4-methylphenyl)-3-phenylsulfonyl-8-azabicyclo[3.2.1]octane-8-carboxamide,
N-(4-isopropylphenyl)-3-phenylsulfonyl-8-azabicyclo[3.2.1]octane-8-carboxamide,
N-(3-trifluoromethylphenyl)-3-phenylsulfonyl-8-azabicyclo[3.2.1]octane-8-carboxamide,
N-(2-trifluoromethylphenyl)-3-phenylsulfonyl-8-azabicyclo[3.2.1]octane-8-carboxamide,
N-(3,5-di-trifluoromethylphenyl)-3-phenylsulfonyl-8-azabicyclo[3.2.1]octane-8-carboxamide,
N-(4-cyclohexylphenyl)-3-phenylsulfonyl-8-azabicyclo[3.2.1]octane-8-carboxamide,
N-(2-methoxyphenyl)-3-phenylsulfonyl-8-azabicyclo[3.2.1]octane-8-carboxamide,
N-(3-methoxyphenyl)-3-phenylsulfonyl-8-azabicyclo[3.2.1]octane-8-carboxamide,
N-(4-methoxyphenyl)-3-phenylsulfonyl-8-azabicyclo[3.2.1]octane-8-carboxamide,
N-(4-isopropoxyphenyl)-3-phenylsulfonyl-8-azabicyclo[3.2.1]octane-8-carboxamide,
3-phenylsulfonyl-N-(pyridin-2-yl)-8-azabicyclo[3.2.1]octane-8-carboxamide,
3-phenylsulfonyl-N-(pyridin-3-yl)-8-azabicyclo[3.2.1]octane-8-carboxamide,
3-phenylsulfonyl-N-(pyridin-4-yl)-8-azabicyclo[3.2.1]octane-8-carboxamide,
N-(4-chlorophenyl)-3-phenylsulfonyl-8-azabicyclo[3.2.1]octane-8-carboxamide,
N-biphenyl-4-yl-3-phenylsulfonyl-8-azabicyclo[3.2.1]octane-8-carboxamide,
3-phenylsulfonyl-N-[4-(1H-pyrazol-3-yl)phenyl]-8-azabicyclo[3.2.1]octane-8-carboxamide,
3-phenylsulfonyl-N-[4-(1,3,4-thiadiazol-2-yl)phenyl]-8-azabicyclo[3.2.1]octane-8-carboxamide,
3-phenylsulfonyl-N-[6-(trifluoromethyl)pyridin-3-yl]-8-azabicyclo[3.2.1]octane-8-carboxamide,
3-phenylsulfonyl-N-[5-(trifluoromethyl)pyridin-3-yl]-8-azabicyclo[3.2.1]octane-8-carboxamide,
3-(pyridin-2-ylsulfonyl)-N-[5-(trifluoromethyl)pyridin-2-yl)]-8-azabicyclo[3.2.1]octane-8-carboxamide,
3-(pyrimidin-2-ylsulfonyl)-N-[5-(trifluoromethyl)pyridin-2-yl)]-8-azabicyclo[3.2.1]octane-8-carboxamide,
N-(4-isopropylphenyl)-3-(pyridin-2-ylsulfonyl)-8-azabicyclo[3.2.1]octane-8-carboxamide,
N-(4-isopropylphenyl)-3-(pyrimidin-2-ylsulfonyl)-8-azabicyclo[3.2.1]octane-8-carboxamide,
3-(4H-1,2,4-triazol-3-ylsulfonyl)-N-[4-(trifluoromethyl)phenyl]-8-azabicyclo[3.2.1]octane-8-carboxamide,
3-(1,3-thiazol-2-ylsulfonyl)-N-[4-(trifluoromethyl)phenyl]-8-azabicyclo[3.2.1]octane-8-carboxamide,
N-(4-tert-butylphenyl)-3-(pyridin-2-ylsulfonyl)-8-azabicyclo[3.2.1]octane-8-carboxamide, and the like. More preferably recommended are:
3-phenylsulfonyl-N-[(4-trifluoromethyl)phenyl]-8-azabicyclo[3.2.1]octane-8-carboxamide,
3-(4-fluorophenyl)sulfonyl-N-[(4-trifluoromethyl)phenyl]-8-azabicyclo[3.2.1]octane-8-carboxamide,
3-(pyridin-2-ylsulfonyl)-N-[(4-trifluoromethyl)phenyl]-8-azabicyclo[3.2.1]octane-8-carboxamide,
3-(pyrimidin-2-ylsulfonyl)-N-[(4-trifluoromethyl)phenyl]-8-azabicyclo[3.2.1]octane-8-carboxamide,
N-(4-isopropylphenyl)-3-phenylsulfonyl-8-azabicyclo[3.2.1]octane-8-carboxamide,
3-phenylsulfonyl-N-[6-(trifluoromethyl)pyridin-3-yl]-8-azabicyclo[3.2.1]octane-8-carboxamide,
3-phenylsulfonyl-N-[5-(trifluoromethyl)pyridin-3-yl]-8-azabicyclo[3.2.1]octane-8-carboxamide,
3-(pyrimidin-2-ylsulfonyl)-N-[5-(trifluoromethyl)pyridin-2-yl)]-8-azabicyclo[3.2.1]octane-8-carboxamide,
N-(4-isopropylphenyl)-3-(pyridin-2-ylsulfonyl)-8-azabicyclo[3.2.1]octane-8-carboxamide,
N-(4-isopropylphenyl)-3-(pyrimidin-2-ylsulfonyl)-8-azabicyclo[3.2.1]octane-8-carboxamide, and
N-(4-tert-butylphenyl)-3-(pyridin-2-ylsulfonyl)-8-azabicyclo[3.2.1]octane-8-carboxamide.

Production Method for a Compound Represented by Formula (I)

The compound of the invention can be produced by the below-mentioned production methods or the methods shown in the Examples, for example. However, the production method for the compound of the invention is not limited to such reaction examples.

Production Method 1

A compound represented by formula (I-1) can be prepared as follows.

Scheme 1

[Chemical Formula 2]

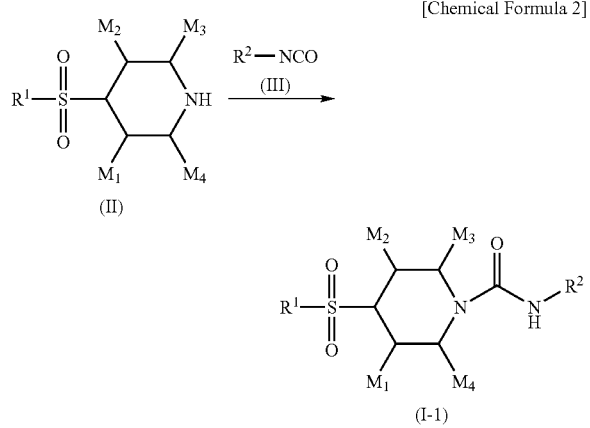

[In the formulae, the symbols are as defined above.]

A compound represented by formula (II) and a compound represented by formula (III) are condensed in an organic solvent to produce a compound represented by formula (I-1).

The amount of compound represented by formula (III) used is 1 to 5 mol, for example, and preferably 1.2 to 1.5 mol per mol of the compound represented by formula (II).

Examples of organic solvents include methylene chloride, chloroform, tetrahydrofuran, ethyl ether, dioxane, dimethylsulfoxide, dimethylformamide, pyridine, and the like.

The reaction temperature is 0 to 100° C., for example, and is preferably room temperature to 50° C. The reaction is usually completed within 10 minutes to 5 hours.

The compound represented by formula (III) may be a commercially available product.

Further, in the reaction, in place of the compound represented by formula (III), a compound represented by formula (IV) may be used in the presence of a base catalyst:

[Chemical Formula 3]

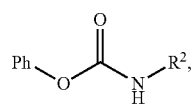

[wherein Ph represents phenyl, and $R^2$ is as defined above.]

The reaction conditions in the case of using a compound represented by formula (IV) are the same as above.

Examples of base catalysts include triethylamine, diisopropylethylamine, N-methylmorpholine, and the like. The amount thereof used is 1.0 to 5.0 mol per mol of the compound represented by formula (II), for example.

Production Method 2

A compound represented by formula (II) can be prepared as follows.

Scheme 2

[Chemical Formula 4]

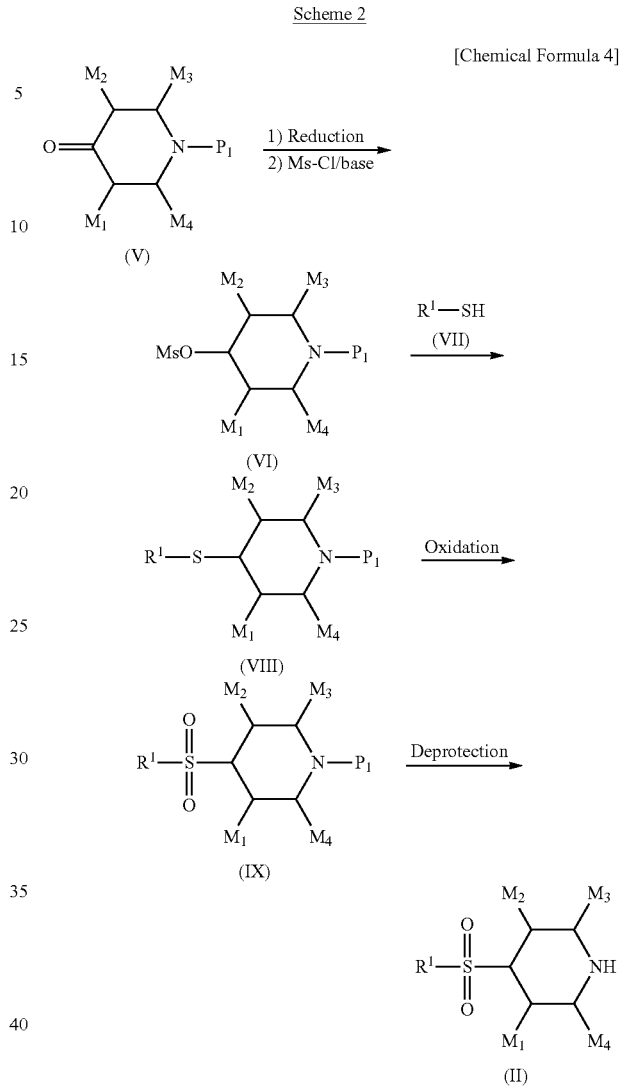

[In the formulae, $P^1$ represents a protecting group, and other symbols are as defined above.]

A compound represented by formula (V) is reduced in an organic solvent in the presence of a reducing agent to convert the ketone moiety into a hydroxy group, and the obtained compound is mesylated by a known method using mesyl chloride to give a compound represented by formula (VI).

Examples of reducing agents include lithium borohydride, sodium borohydride, lithium aluminum hydride, and the like. Preferably, lithium borohydride, sodium borohydride, and the like are recommended.

The amount of reducing agent used is 1 to 20 mol, for example, and preferably 1.2 to 1.5 mol per mol of the compound represented by formula (V).

Examples of organic solvents for the reduction reaction include tetrahydrofuran, dioxane, ethanol, water, and the like.

The reaction temperature is −78 to 50° C., for example, and is preferably 0° C. to room temperature. The reaction is usually completed within 1 to 5 hours.

Instead of mesylation herein, tosylation using p-toluenesulfonyl chloride, benzenesulfonylation using benzenesulfonyl chloride, or the like may also be employed.

Subsequently, the compound represented by formula (VI) is reacted with a compound represented by formula (VII) in an organic solvent to produce a compound represented by formula (VIII).

The amount of compound represented by formula (VII) used is 1 to 5 mol, for example, and preferably 1.2 to 1.5 mol per mol of the compound represented by formula (VI).

Examples of organic solvents include tetrahydrofuran, dioxane, dimethylformamide, dimethylsulfoxide, and the like, and mixed solvents thereof.

The reaction temperature is 0 to 150° C., for example, and is preferably 80 to 120° C. The reaction is usually completed within 10 minutes to 14 hours.

Examples of compounds represented by formula (VII) include benzenethiol, 4-fluorobenzenethiol, 2-methoxybenzenethiol, 3-methoxybenzenethiol, 4-methoxybenzenethiol, 2-chlorobenzenethiol, 3-chlorobenzenethiol, 4-chlorobenzenethiol, 2-mercaptopyridine, 3-mercaptopyridine, 4-mercaptopyridine, 2-mercaptopyrimidine, 1,2,4-triazol-3-ylbenzenethiol, thiazol-2-ylbenzenethiol, and the like.

Subsequently, the compound represented by formula (VIII) is oxidized with an oxidizing agent in an organic solvent to produce a compound represented by formula (IX).

Examples of oxidizing agents include potassium permanganate, sodium periodate, hydrogen peroxide, m-chloroperbenzoic acid, peracetic acid, OXONE®, and the like. Preferably, potassium permanganate is recommended.

The amount of oxidizing agent used is 2 to 20 mol, for example, and preferably 2 to 5 mol per mol of the compound represented by formula (VIII).

Examples of organic solvents include methylene chloride, chloroform, acetic acid, tetrahydrofuran, ethyl ether, dioxane, acetone, and the like.

The reaction temperature is −78 to 50° C., for example, and is preferably 0° C. to room temperature. The reaction is usually completed within 1 to 14 hours.

Subsequently, the protecting group $P^1$ of the compound represented by formula (IX) is removed to give a compound represented by formula (II).

Although deprotection depends on the type of the protecting group, the stability of the target compound (II), and the like, the protecting group can be removed, according to the method described in the literature (see Protective Groups in Organic Synthesis, T. W. Greene, John Wiley & Sons, 1981) or a similar method, by, for example, solvolysis with acid or base, i.e., for example, with 0.01 mol to a large excess of acid, preferably trifluoroacetic acid, formic acid, hydrochloric acid, or the like, or with an equimolar amount to a large excess of base, preferably potassium hydroxide, calcium hydroxide, or the like; chemical reduction using a metal hydride complex; catalytic hydrogenation using a palladium-carbon catalyst, a Raney nickel catalyst, or the like; etc.

Production Method 3

A compound represented by formula (IV) can be prepared as follows.

Scheme 3

[Chemical Formula 5]

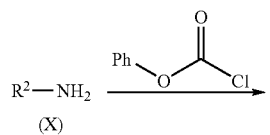

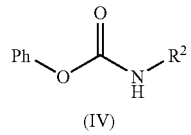
(IV)

[In the formulae, the symbols are as defined above.]

A compound represented by formula (X) and phenyl chloroformate are condensed in an organic solvent in the presence of a base to produce a compound represented by formula (IV).

The amount of phenyl chloroformate used is 1 to 3 mol, for example, and preferably 1.2 to 1.5 mol per mol of the compound represented by formula (X).

Examples of bases include organic bases such as pyridine, triethylamine, diisopropylethylamine, pyridine, 4-dimethylaminopyridine, and the like; inorganic bases such as sodium hydroxide, potassium hydroxide, sodium carbonate, potassium carbonate, sodium hydrogen carbonate, and the like. Preferably, pyridine is recommended.

The amount of base used is 1 to 3 mol, for example, and preferably 1.2 to 1.5 mol per mol of the compound represented by formula (X).

Examples of organic solvents include methylene chloride, chloroform, tetrahydrofuran, ethyl ether, toluene, dimethylformamide, dimethylsulfoxide, and the like, and mixed solvents thereof.

Further, as a solvent that serves as both an organic solvent and a base, an excessive amount of pyridine may also be used.

The compound represented by formula (IV) may be used in place of the compound represented by formula (III) in the production method 1 to prepare a compound represented by formula (I-1).

Production Method 4

The compound represented by formula (I-2) can be prepared as follows.

Scheme 4

[Chemical Formula 6]

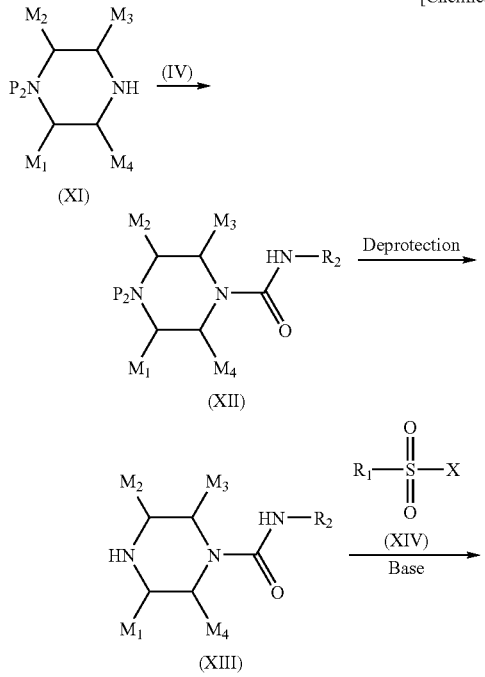

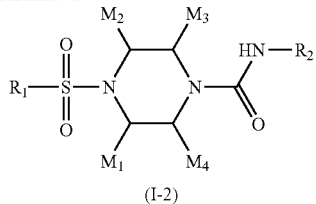

(I-2)

[In the formulae, $P_2$ has the same meaning as $P_1$, X represents halogen, and other symbols are as defined above.]

A compound represented by formula (XI) and a compound represented by formula (IV) are condensed to produce a compound represented by formula (XII). The reaction method may be in accordance with the production method 1. In place of the compound represented by formula (IV), a compound represented by formula (III) may also be used.

The protecting group of the compound represented by formula (XII) is removed to produce a compound represented by formula (XIII). Deprotection may be carried out in accordance with the above method described in "Protective Groups in Organic Synthesis". For example, when X is a Boc group (t-butyloxycarbonyl), deprotection can be achieved by reacting the compound represented by formula (XIII) with 1 to 50 equivalents of hydrogen chloride-ethyl acetate solution at room temperature for 1 to 24 hours.

Subsequently, the compound represented by formula (XIII) and a compound represented by formula (XIV) are reacted in an organic solvent in the presence of a base to produce a compound represented by formula (I-2).

The amount of compound represented by formula (XIV) used is 1 to 3 mol, for example, and preferably 1 to 2 mol per mol of the compound represented by formula (XIII).

Examples of bases include triethylamine, diisopropylethylamine, pyridine, and the like. The amount of base used is 1 to 5 mol, for example, and preferably 1 to 3 mol per mol of the compound represented by formula (XIII).

Examples of organic solvents include methylene chloride, chloroform, tetrahydrofuran, ethyl ether, dioxane, dimethylsulfoxide, dimethylformamide, pyridine, and the like.

The reaction temperature is 0 to 40° C., for example, and is preferably 0 to 30° C. The reaction is usually completed within 1 to 24 hours.

Examples of compounds represented by formula (XIV) include benzenesulfonyl chloride, toluenesulfonyl chloride, pyridinesulfonyl chloride, and the like, and any commercially available product may be used.

In the above reaction, when the reactant has an amino group, an imino group, a carboxyl group, and the like that are not involved in the reaction, then the amino group, the imino group, and the carboxyl group, may be suitably protected, prior to the reaction, with an amino- or imino-protecting group or with a carboxyl-protecting group, followed by removal of the protecting groups after the reaction.

Examples of "amino- or imino-protecting groups" include benzyl, p-methoxybenzyl, 3,4-dimethoxybenzyl, o-nitrobenzyl, p-nitrobenzyl, benzhydryl, trityl; $C_{1-6}$ alkanoyl such as formyl, acetyl, propionyl, butyryl, pivaloyl; benzoyl; arylalkanoyl such as phenylacetyl, phenoxyacetyl; $C_{1-6}$ alkyloxycarbonyl such as methoxycarbonyl, ethoxycarbonyl, propyloxycarbonyl, tert-butoxycarbonyl; aralkyloxycarbonyl such as benzyloxycarbonyl, p-nitrobenzyloxycarbonyl, phenethyloxycarbonyl; $C_{1-6}$ alkylsilyl such as trimethylsilyl, tert-butyldimethylsilyl, and the like. Acetyl, pivaloyl, benzoyl, ethoxycarbonyl, tert-butoxycarbonyl, and the like are particularly preferable.

Examples of "carboxyl-protecting groups" include $C_{1-6}$ alkyl such as methyl, ethyl, propyl, isopropyl, tert-butyl; $C_{1-6}$ haloalkyl such as 2,2,2-trichloroethyl; alkenyl such as 2-propenyl; aralkyl such as benzyl, p-methoxybenzyl, p-nitrobenzyl, benzhydryl, trityl, and the like. Methyl, ethyl, tert-butyl, 2-propenyl, benzyl, p-methoxybenzyl, benzhydryl, and the like are particularly preferable.

A protecting group can be introduced and removed in accordance with the above method described in the literature "Protective Groups in Organic Synthesis" or a similar method.

The thus-obtained compound of formula (I) can be readily isolated and purified by an ordinary isolation procedure, such as solvent extraction, recrystallization, column chromatography, preparative thin-layer chromatography, or the like.

These compounds may be converted into pharmaceutically acceptable salts in the usual manner. The other way around, conversion of salts into free compounds is also possible in the usual manner.

The usefulness of the compound of the invention as a medicine will be demonstrated, for example, by the following pharmacological test examples.

Pharmacological Test Example 1 (LCE Enzyme Activity Inhibition Test)

A test compound was dissolved in dimethylsulfoxide (DMSO) to 10 mM, and further diluted with DMSO to prepare a 1000-fold concentrated solution, compared with the evaluated concentration. The LCE enzyme activity inhibition test was carried out according to a modification of the method of Moon (J. Biol. Chem., Vol. 276, pp. 45358-45366 (2001)) et al. Specifically, the diluted test compound was added to a 96-well assay plate (Corning, 96-well assay block) at 1.0 μL per well, and then 50 μL of phosphate buffer solution (100 mM potassium phosphate buffer solution (pH 6.5)), 25 μL of substrate solution (100 mM potassium phosphate buffer solution (pH 6.5)), 4.0 μM rotenone, 80 μM fatty acid free bovine serum albumin, 160 μM palmitoyl-CoA 80 μM malonyl-CoA, and 3.5 μM [$^{14}$C]-malonyl-CoA (1.92 GBq/mmol, manufactured by Amersham) were added to each well. Further, 25 μL of enzyme solution (100 mM potassium phosphate buffer solution (pH 6.5), 100 μg/mL human LCE) was added thereto. The plate was hermetically closed at the top with a seal, and then incubated with gentle agitation by shaking at 37° C. for 90 minutes. Subsequently, 100 μL of 5N HCl was added to each well, and the assay plate was agitated for 5 minutes at room temperature to stop the enzymatic reaction and also hydrolyze acyl-CoA. Subsequently, the enzymatic reaction solution of each well was adsorbed on each well of a 96-well GF/C filter plate (PerkinElmer, UniFilter 96 GF/C) that had been previously dipped in water. The wells were washed with water to remove unabsorbed malonyl-CoA, and the GF/C filter plate was dried at 50° C. for 60 minutes. Subsequently, 30 μL of scintillator (PerkinElmer, MicroScinti 0) was added to each well, and the plate was sealed at the top. Using a microplate scintillation counter (PerkinElmer, TopCount), the radiation activity of the fixed [$^{14}$C] was measured and obtained as the enzyme activity. The human LCE enzyme inhibitory activity of a test compound was calculated based on the radio activity in the well containing test-compound-free DMSO as a control. Compounds of the invention were examined according to this assay. As a result, the compounds inhibited the activity of human LCE. The results are shown in Table 1.

TABLE 1

| Example No. | IC50 (nM) |
|---|---|
| 1 | 98 |
| 2 | 108 |
| 9 | 92 |
| 12 | 100 |
| 16 | 29 |
| 32 | 127 |
| 33 | 103 |
| 35 | 194 |
| 36 | 32 |
| 37 | 22 |
| 40 | 125 |

Compounds of the invention may be administered orally or parenterally. As formulated into a dosage form suitable for the administration route, the compound of the invention can be used as a preventive or a remedy for hypertension, angina pectoris, cardiac insufficiency, myocardial infarction, stroke, claudication, diabetic nephropathy, diabetic retinopathy, visual loss, electrolyte abnormality, atherosclerosis, and like circulatory diseases; bulimia, diabetic neuropathy, and like central neurological diseases; metabolic syndrome, obesity, diabetes, insulin resistance, hyperlipidemia, hypercholesterolemia, hypertriglyceridemia, dyslipidemia, non-alcoholic fatty liver disease, inappropriate hormone secretion, gout, fatty liver, and like metabolic diseases; menstrual disorder, sexual dysfunction, and like reproductive system diseases; hepatic dysfunction, pancreatitis, cholecystitis, gastroesophageal reflux, and like digestive diseases; obesity hypoventilation syndrome (Pickwickian syndrome), sleep apnea syndrome, and like respiratory diseases; infectious diseases caused by bacteria, fungi, and parasites; neoplasm, arthritis, skin ulcer, and like inflammatory diseases; and the like.

One aspect of the invention provides a method for treating or preventing diseases, illnesses, or conditions caused by the modulation of LCE, comprising administering a therapeutically or prophylactically effective amount of the compound of the invention to a subject in need thereof.

Another aspect of the invention provides a method for treating or preventing metabolic syndrome, fatty liver, hyperlipidemia, dyslipidemia, non-alcoholic fatty liver disease, obesity, diabetes, bulimia, neoplasm, or an infectious disease, comprising administering a therapeutically or prophylactically effective amount of the compound of the invention to a subject in need thereof.

Another aspect of the invention provides a method for treating or preventing diabetes, comprising administering a therapeutically or prophylactically effective amount of the compound of the invention to a subject in need thereof.

Another aspect of the invention provides a method for treating or preventing obesity, comprising administering a therapeutically or prophylactically effective amount of the compound of the invention to a subject in need thereof.

Another aspect of the invention provides a method for treating or preventing an obesity-related disease selected from the group consisting of overeating, bulimia, hypertension, elevated plasma insulin level, insulin resistance, hyperlipidemia, endometrial cancer, breast cancer, prostate cancer, colon cancer, kidney cancer, osteoarthritis, obstructive sleep apnea, heart disease, abnormal heart rhythms, arrhythmia, myocardial infarction, congestive heart failure, coronary heart disease, sudden death, stroke, polycystic ovary disease, craniopharyngioma, metabolic syndrome, insulin resistance syndrome, sexual and reproductive dysfunction, infertility, hypogonadism, hirsutism, obesity-related gastroesophageal reflux, obesity hypoventilation syndrome (Pickwickian syndrome), inflammation, systemic vasculitis, atherosclerosis, hypercholesterolemia, hyperuricemia, lumbago, inflammation, systemic vasculitis, atherosclerosis, hypercholesterolemia, hyperuricemia, lumbago, gallbladder disease, gout, constipation, irritable bowel syndrome, inflammatory bowel syndrome, cardiac hypertrophy, and left ventricular hypertrophy, wherein the method comprising administering a therapeutically or prophylactically effective amount of the compound of the invention to a subject in need thereof.

Another aspect of the invention provides a method for treating or preventing hyperlipidemia or dyslipidemia, comprising administering a therapeutically or prophylactically effective amount of the compound of the invention to a subject in need thereof.

Another aspect of the invention provides a method for caloric intake, comprising administering a therapeutically or prophylactically effective amount of the compound of the invention to a subject in need thereof.

Another aspect of the invention provides a method for reducing food intake, comprising administering a therapeutically or prophylactically effective amount of the compound of the invention to a subject in need thereof.

Another aspect of the invention provides a method for increasing satiety, comprising administering a therapeutically or prophylactically effective amount of the compound of the invention to a subject in need thereof.

Another aspect of the invention provides a method for reducing appetite, comprising administering a therapeutically or prophylactically effective amount of the compound of the invention to a subject in need thereof.

The invention also relates to a method for treating or preventing obesity, comprising administering the compound of the invention in combination with a therapeutically or prophylactically effective amount of another drug known to be useful in the treatment or prevention of the condition.

The invention also relates to a method for treating or preventing diabetes, comprising administering the compound of the invention in combination with a therapeutically or prophylactically effective amount of another drug known to be useful in the treatment or prevention of the condition.

The invention also relates to a method for treating or preventing hyperlipidemia or dyslipidemia, comprising administering the compound (I) of the invention or a pharmaceutically acceptable salt thereof in combination with a therapeutically or prophylactically effective amount of another drug known to be useful in the treatment or prevention of the condition.

Another aspect of the invention relates to a pharmaceutical composition comprising the compound of the invention and a pharmaceutically acceptable carrier.

Yet another aspect of the invention relates to the compound of the invention for use as a medicament.

Yet another aspect of the invention relates to the use of the compound of the invention for manufacturing a medicine useful in the treatment, prevention, or suppression of an LCE-attributable disease in a subject in need thereof.

Yet another aspect of the invention relates to the use of the compound of the invention for manufacturing a medicament useful in the treatment or prevention of metabolic syndrome, hyperlipidemia, dyslipidemia, non-alcoholic fatty liver disease, obesity, diabetes, bulimia, neoplasm, or an infectious disease in a subject in need thereof.

Yet another aspect of the invention relates to the use of the compound of the invention for manufacturing a medicament useful in the treatment or prevention of obesity in a subject in need thereof.

Yet another aspect of the invention relates to the use of the compound of the invention for manufacturing a medicament useful in the treatment or prevention of diabetes in a subject in need thereof.

Yet another aspect of the invention relates to the use of the compound of the invention for manufacturing a medicament useful in the treatment or prevention of hyperlipidemia or dyslipidemia in a subject in need thereof.

Yet another aspect of the invention relates to the use of a therapeutically effective amount of the compound of the invention and a therapeutically effective amount of a drug selected from the group consisting of an insulin sensitizer, an insulin mimetic, a sulfonylurea, an α-glucosidase inhibitor, a dipeptidyl peptidase-4 (DPP-4 or DP-IV) inhibitor, a glucagon-like peptide-1 (GLP-1) agonist, an HMG-CoA reductase inhibitor, a serotonin-like substance, a β3-adrenoreceptor agonist, a neuropeptide Y1 antagonist, a neuropeptide Y2 agonist, a neuropeptide Y5 antagonist, a pancreatic lipase inhibitor, a cannabinoid CB1 receptor antagonist or inverse agonist, a melanin-concentrating hormone receptor agonist, a melanocortin-4 receptor agonist, a bombesin receptor subtype 3 agonist, a ghrelin antagonist, PYY, $PYY_{3-36}$, and an NK-1 antagonist, or a pharmaceutically acceptable salt thereof, for manufacturing a medicament useful in the treatment, control, or prevention of obesity, diabetes, a diabetes-related disease, or an obesity-related disease in a subject in need thereof.

Yet another aspect of the invention relates to the use of a therapeutically effective amount of the compound of the invention and a therapeutically effective amount of a drug selected from the group consisting of an insulin sensitizer, an insulin mimetic, a sulfonylurea, an α-glucosidase inhibitor, a dipeptidyl peptidase-4 (DPP-4 or DP-IV) inhibitor, a glucagon-like peptide-1 (GLP-1) agonist, an HMG-CoA reductase inhibitor, a serotonin-like substance, a β3-adrenoreceptor agonist, a neuropeptide Y1 antagonist, a neuropeptide Y2 agonist, a neuropeptide Y5 antagonist, a pancreatic lipase inhibitor, a cannabinoid CB1 receptor antagonist or inverse agonist, a melanin-concentrating hormone receptor agonist, a melanocortin-4 receptor agonist, a bombesin receptor subtype 3 agonist, a ghrelin antagonist, PYY, $PYY_{3-36}$, and an NK-1 antagonist, or a pharmaceutically acceptable salt thereof, for manufacturing a medicament for use in the treatment or prevention of obesity, diabetes, a diabetes-related disease, or an obesity-related disease, wherein the effective amount of the compound of the invention and the effective amount of the drug are used simultaneously or separately.

Yet another aspect of the invention relates to a combination product comprising a therapeutically effective amount of the compound of the invention and a therapeutically effective amount of a drug selected from the group consisting of an insulin sensitizer, an insulin mimetic, a sulfonylurea, an α-glucosidase inhibitor, a dipeptidyl peptidase-4 (DPP-4 or DP-IV) inhibitor, a glucagon-like peptide-1 (GLP-1) agonist, an HMG-CoA reductase inhibitor, a serotonin-like substance, a β3-adrenoreceptor agonist, a neuropeptide Y1 antagonist, a neuropeptide Y2 agonist, a neuropeptide Y5 antagonist, a pancreatic lipase inhibitor, a cannabinoid CB 1 receptor antagonist or inverse agonist, a melanin-concentrating hormone receptor agonist, a melanocortin-4 receptor agonist, a bombesin receptor subtype 3 agonist, a ghrelin antagonist, PYY, $PYY_{3-36}$, and an NK-1 antagonist, or a pharmaceutically acceptable salt thereof, for simultaneous, separate, or sequential use in obesity, diabetes, a diabetes-related disease, or an obesity-related disease.

Yet another aspect of the invention relates to the use of a therapeutically effective amount of the compound of the invention and a therapeutically effective amount of a drug selected from the group consisting of simvastatin, mevastatin, ezetimibe, atorvastatin, sitagliptin, metformin, sibutramine, orlistat, Qnexa (trade name), and phentermine, or a pharmaceutically acceptable salt thereof, for manufacturing a medicament useful in the treatment, control, or prevention of obesity, diabetes, a diabetes-related disease, or an obesity-related disease in a subject in need thereof.

In clinical use of the compound of the invention, the compound may be formulated into various preparations by adding pharmaceutically acceptable additives thereto in accordance with the administration route, and then administered. As such additives, various additives ordinarily used in the field of pharmaceutical preparations are usable, examples thereof including gelatin, lactose, sucrose, titanium oxide, starch, crystalline cellulose, methylcellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, palmitoleic acid, light silicic acid anhydride, talc, vegetable oil, benzyl alcohol, gum arabic, propylene glycol, polyalkylene glycol, cyclodextrin, hydroxypropyl cyclodextrin, and the like.

As mixtures with such additives, various dosage forms are formulated, including, for example, tablets, capsules, granules, powders, suppositories, and like solid preparations; syrups, elixirs, injections, and like liquid preparations; and the like. These preparations can be produced by any method known in the field of pharmaceutical preparations. Liquid preparations may be those that are dissolved or suspended in water or a like suitable medium before use. In case of injections, such preparations may be dissolved or suspended in a physiological saline solution or a glucose solution as required. Further, a buffer and a preservative may also be added thereto.

The compound of the invention is effective for plants and animals in need of treatment with the compound, including humans and other mammals. Preferred examples of mammals are humans, and they may be male or female. The mammals other than humans are, for example, companion animals such as dogs, cats, and the like. The compound of the invention is also effective for obesity or obesity-related diseases in such dogs, cats, and the like. Whether treatment with the compound of the invention is necessary can be readily determined by an ordinary physician, veterinarian, or clinician.

In clinical use of the compound of the invention, the dosage thereof and the frequency of administration differ depending on the sex, age, and body weight of the patient, the degree of symptom, the kind and scope of desired treatment effects, and the like. In general, for a human adult, in the case of oral administration, a daily dose of 0.01 to 100 mg/kg, preferably 0.03 to 1 mg/kg, is administered preferably in one to several doses. In the case of parenteral administration, a daily dose of 0.001 to 10 mg/kg, preferably 0.001 to 0.1 mg/kg, and more preferably 0.01 to 0.1 mg/kg is administered preferably in one to several doses.

For oral administration, tablets containing 1.0 to 1000 mg of the active ingredient, especially, for adjusting the dosage according to the symptom of the patient to be treated, 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient, are preferable. The compound may be administered in one to four doses per day, and preferably one or two doses per day.

In case where the compound of the invention is applied to the treatment or prevention of obesity and/or diabetes and/or hyperlipidemia and/or dyslipidemia and/or non-alcoholic fatty liver disease, or other diseases, generally, satisfactory results are obtained when the compound of the invention is administered in a daily dose of about 0.1 mg to about 100 mg per kg of animal body weight, preferably in a single dose or in two to six divided doses a day, or as a sustained-release preparation. For most of the large mammals, the total daily dose is about 1.0 mg to about 1000 mg, and preferably about 1 mg to about 50 mg. In the case of a 70 kg adult human, the total daily dose will normally be about 7 mg to about 350 mg. Such prescribed dosages may be adjusted to maximize the therapeutic effect.

An ordinary physician, veterinarian, or clinician can readily determine and treat the effective dosage necessary to treat, prevent, retard, suppress, or halt the progression of the disease.

These preparations may contain the compound of the invention in a proportion of 1.0 to 100 wt %, preferably 1.0 to 60 wt %, by weight of the total preparations. These preparations may also contain other compounds that are therapeutically effective.

The compound of the invention may be used in combination with other agents that are useful in the treatment of diseases, including hypertension, angina pectoris, cardiac insufficiency, myocardial infarction, stroke, claudication, diabetic nephropathy, diabetic retinopathy, visual loss, electrolyte abnormality, atherosclerosis, and like circulatory diseases; bulimia, diabetic neuropathy, and like central neurological diseases; metabolic syndrome, obesity, diabetes, insulin resistance, hyperlipidemia, hypercholesterolemia, hypertriglyceridemia, dyslipidemia, non-alcoholic fatty liver disease, inappropriate hormone secretion, gout, fatty liver, and like metabolic diseases; menstrual disorder, sexual dysfunction, and like reproductive system diseases; hepatic dysfunction, pancreatitis, cholecystitis, gastroesophageal reflux, and like digestive diseases; obesity hypoventilation syndrome (Pickwickian syndrome), sleep apnea syndrome, and like respiratory diseases; infectious diseases caused by bacteria, fungi, and parasites; neoplasm; arthritis, skin ulcer, and like inflammatory diseases; and the like. The individual ingredients of the combination may be administered, during the treatment period, at different time points or simultaneously as separate preparations or as a single preparation. Accordingly, the invention should be interpreted to encompass all mode of administrations at the same time or at different time, and the administration in the invention should be so interpreted. In principle, the range of combinations of the compound of the invention and other agents useful in the treatment of the above diseases encompasses combinations with any pharmaceutical preparation useful in the treatment of the above diseases.

The combination includes not only the combination of the composition of the invention and one other active substance but also the combination with two or more other active substances. There are a number of examples of combinations of the compound of the invention and one, two, or more active substances selected from the remedies for the above diseases. For example, for the treatment, control, and prevention of metabolic syndrome, a combination of the compound of the invention and one, two, or more active substances selected from hypolipidemic agents, lipid-lowering agents, and antidiabetic agents is useful. In particular, a composition containing, in addition to an antidiabetic agent and/or a hypolipidemic agent or a lipid-lowering agent, an antiobesity agent and an antihypertensive agent provides a synergistic effect in the treatment, control, or prevention of metabolic syndrome.

Examples of drugs for use in combination with the compound of the invention include ACAT inhibitors, α-blockers, aldose reductase inhibitors, α-amylase inhibitors, angiotensin-converting enzyme inhibitors, angiotensin receptor antagonists, anion exchange resins, anorectics, antioxidants, antiplatelets, β-blockers, biguanides, calcium antagonists, CB1 receptor inverse agonists/antagonists, CETP inhibitors, cholesterol absorption inhibitors, DGAT inhibitors, DP-IV inhibitors, diuretic agents, eicosapentaenoic acid, endothelin antagonists, FLAP inhibitors, FXR modulators, Ghrelin antagonists, GLP-1 agonists, GLP-1 secretagogues, glucagon antagonists, glucokinase activators, glucocorticoid receptor ligands, α-glucosidase inhibitors, GPAT inhibitors, histamine-H3 receptor ligands, HMG-CoA reductase inhibitors, HSD inhibitors, insulin and insulin mimetics, kinase inhibitors such as VEGF inhibitors, PDGF inhibitors, and the like, leptin, lipase inhibitors, 5-LO inhibitors, LXR ligands, melanocortin agonists, MCH antagonists, MTTP inhibitors, orexin antagonists, opioid antagonists, neuropeptide Y antagonists, nicotinic acid agonists, PPAR ligands, PTP-1B inhibitors, SCD-1 inhibitors, serotonin transporter inhibitors, SGLT inhibitors, SUR ligands, thyroid hormone agonists, UCP activators, VPAC receptor agonists, and the like.

Advantage of the Invention

The compound of the invention has excellent LCE inhibitory effect, and is useful as a remedy for various LCE-associated diseases, such as circulatory diseases, neurological diseases, metabolic diseases, reproductive system diseases, digestive diseases, neoplasms, infectious diseases, and the like, or as a herbicide.

BEST MODE FOR CARRYING OUT THE INVENTION

Hereinafter, the present invention will be described in further detail with reference to the Reference Examples and Examples; however, the invention is not limited to these examples.

EXAMPLES

In thin-layer chromatography, Silica gel$_{60}$F$_{254}$ (Merck) was used as the plate, and a UV detector was used for detection. As a silica gel for the column, Wakogel™ C-300 or C-200 (Wako Pure Chemical Industries), a FLASH+ cartridge (Biotage), or Chromatorex (FUJI SILYSIA CHEMICAL) was used. MS spectra were measured using ZQ2000 (Waters). When measuring NMR spectra in a heavy dimethylsulfoxide solution, dimethylsulfoxide was employed as the internal standard, and the spectra were measured using a JNM-AL400 (JEOL), Mercury 400 (400 MHz; Varian), or Inova 400 (400 MHz; Varian) spectrometer. All the δ values were expressed in ppm.

The meanings of the abbreviations in the NMR measurement are shown below.
s: singlet
d: doublet
dd: double doublet
t: triplet
dt: double triplet
q: quartet
m: multiplet
br: broad
J: coupling constant
Hz: hertz
DMSO-d$_6$: heavy dimethylsulfoxide

Reference Example

Production of tert-butyl 3-oxo-8-azabicyclo[3.2.1]octane-8-carboxylate (1) Production of tert-butyl 3-oxo-8-azabicyclo[3.2.1]octane-8-carboxylate To a dichloroethane (200 mL) solution of tropinone (25.1 g) was added 1-chloroethyl chloroformate (29.4 mL), and the mixture was refluxed for 2 hours. The solvent was distilled off under reduced pressure, methanol (200 mL) was added thereto, and the mixture was refluxed for 14 hours. The reaction mixture was condensed to give a crude product (25.0 g) of 8-azabicyclo[3.2.1]octan-3-one hydrochloride. To an acetonitrile solution (200 mL) of 8-azabicyclo[3.2.1]octan-3-one hydrochloride (8.1 g) were added triethylamine (20.9 mL), dimethylaminopyridine (611 mg), and di-tert-butyl dicarbonate (12.0 g), and the mixture was stirred at room temperature for 14 hours. The solvent was distilled off under reduced pressure, and a saturated aqueous ammonium chloride solution was added thereto, followed by extraction with diethyl ether. The organic layer was dried over sodium sulfate. After filtration, the solvent was distilled off under reduced pressure. The concentrated residue was purified by silica gel flash chromatography (hexane/ethyl acetate=4/1 to 1/2) to give the title compound as a colorless solid (11.17 g).

$^1$HNMR (400 MHz, CDCl$_3$, δppm): 1.50 (9H, s), 1.65-1.69 (2H, m), 2.05-2.13 (2H, m), 2.29-2.38 (2H, m), 2.51-2.80 (2H, m), 4.36-4.58 (2H, m)

(2) Production of 3-exo-hydroxy-8-azabicyclo[3.2.1]octane-8-carboxylic acid tert-butyl ester To an ethanol solution (100 mL) of sodium borohydride (2.27 g) were added water (100 mL) and cerium chloride 6-hydrate (22.35 g) at 0° C., and the mixture was stirred for 1 hour. tert-Butyl 3-oxo-8-azabicyclo[3.2.1]octane-8-carboxylate (11.17 g) was added thereto at the same temperature, stirred at 0° C. for 1 hour, then heated to room temperature, and stirred for 14 hours. The solvent was distilled off under reduced pressure, and a saturated aqueous ammonium chloride solution was added thereto, followed by extraction with diethyl ether. The organic layer was dried over sodium sulfate. After filtration, the solvent was distilled off under reduced pressure. The concentrated residue was purified by silica gel flash chromatography (hexane/ethyl acetate=4/1 to 1/2) to give the title compound as a colorless solid (8.58 g).

$^1$HNMR (400 MHz, CDCl$_3$, ppm): 1.31 (1H, d, J=5.9 Hz), 1.47 (9H, s), 1.58-1.67 (3H, m), 1.88-2.01 (4H, m), 4.06-4.14 (1H, m), 4.15-4.33 (2H, m)

(3) Production of 3-exo-methanesulfonyloxy-8-azabicyclo[3.2.1]octane-8-carboxylic acid tert-butyl ester To a tetrahydrofuran (500 mL) solution of 3-exo-hydroxy-8-azabicyclo[3.2.1]octane-8-carboxylic acid tert-butyl ester (49.37 g) were added triethylamine (45.4 mL) and methanesulfonyl chloride (20.17 mL) at 0° C., and the mixture was stirred for 1 hour. Water was added to the reaction mixture, followed by extraction with ethyl acetate. The organic layer was dried over sodium sulfate. After filtration, the solvent was distilled off under reduced pressure. The concentrated residue was purified by silica gel flash chromatography (hexane/ethyl acetate=4/1 to 0:1) to give the title compound as a colorless solid (59.44 g).

$^1$HNMR (400 MHz, CDCl$_3$, δppm): 1.48 (9H, s), 1.53-1.62 (2H, m), 1.64-1.72 (2H, m), 1.78-2.18 (5H, m), 3.01 (3H, s), 4.18-4.37 (1H, m), 5.02 (1H, m)

(4) tert-Butyl 3-phenylthio-8-azabicyclo[3.2.1]octane-8-carboxylate

To a DMF (5 mL) solution of 3-exo-methanesulfonyloxy-8-azabicyclo[3.2.1]octane-8-carboxylic acid tert-butyl ester (279 mg) were added thiophenol (132 mg) and potassium carbonate (207 mg), and the mixture was stirred at 80° C. for 5 hours. Water was added to the reaction solution, followed by extraction with ethyl acetate. The organic layer was dried over sodium sulfate. After filtration, the solvent was distilled off under reduced pressure. The concentrated residue was purified by silica gel flash chromatography (hexane/ethyl acetate=4/1 to 1/2) to give the title compound as a colorless solid (181 mg).

$^1$HNMR (400 MHz, CDCl$_3$, δppm): 1.45 (9H, s), 1.51-1.64 (2H, m), 1.82 (2H, d, J=12.0 Hz), 1.96-2.03 (2H, m), 2.15-2.34 (2H, m), 3.64 (1H, t, J=8.0 Hz), 4.10-4.34 (2H, m), 7.19-7.37 (4H, m), 7.48-7.52 (1H, m)

(5) tert-Butyl 3-phenylsulfonyl-8-azabicyclo[3.2.1]octane-8-carboxylate

To an acetone (10 mL) solution of tert-butyl 3-phenylthio-8-azabicyclo[3.2.1]octane-8-carboxylate (181 mg) were added acetic acid (26 μL) and an aqueous potassium permanganate (190 mg) solution (10 mL) at room temperature, and the mixture was stirred for 14 hours. A 10% aqueous sodium sulfite solution was added to the reaction solution, and then filtered through Celite. The solvent was distilled off under reduced pressure, followed by extraction with chloroform. The organic layer was dried over sodium sulfate. After filtration, the solvent was distilled off under reduced pressure to give a crude product of the title compound as a colorless solid (174 mg).

$^1$HNMR (400 MHz, CDCl$_3$, δppm): 1.42 (9H, s), 1.80-2.04 (6H, m), 2.27-2.40 (2H, m), 3.05-3.16 (1H, m), 4.21-4.30 (2H, m), 7.57 (2H, t, J=8.0 Hz), 7.66 (1H, t, J=8.0 Hz), 7.84-7.88 (2H, m)

(6) 3-Phenylsulfonyl-8-azabicyclo[3.2.1]octane hydrochloride

To a methanol (5 mL) solution of tert-butyl 3-phenylsulfonyl-8-azabicyclo[3.2.1]octane-8-carboxylate (174 mg) was added a 4N-hydrogen chloride methanol solution, and the mixture was stirred at 60° C. for 3 hours. The solvent was distilled off under reduced pressure, and the resulting solid was washed with diethyl ether to give a crude product of the title compound as a colorless solid (141 mg).

$^1$HNMR (400 MHz, CDCl$_3$, δppm): 1.90-2.15 (6H, m), 2.32-2.45 (2H, m), 3.70-3.8 (1H, m), 3.90-4.10 (2H, m), 7.30-7.95 (5H, m)

Example 1

Production of 3-phenylsulfonyl-N-[(4-trifluoromethyl)phenyl]-8-azabicyclo[3.2.1]octane-8-carboxamide To a chloroform solution (5 mL) of 3-phenylsulfonyl-8-azabicyclo[3.2.1]octane hydrochloride (29 mg) were added triethylamine (28 μL) and 4-(trifluoromethyl)phenyl isocyanate (28 mg), and the mixture was stirred at 80° C. for 1 hours.

The reaction mixture was partitioned between water and ethyl acetate, and the organic layer was dried over anhydrous magnesium sulfate. The solvent was distilled off, and the residue was purified by preparative thin-layer chromatography (chloroform/methanol=10/1) to give the title compound (19 mg) as a colorless solid.

$^1$HNMR (400 MHz, CDCl$_3$, δppm): 1.98-2.14 (6H, m), 2.39-2.49 (2H, m), 3.18-3.28 (1H, m), 4.31-4.39 (2H, m), 6.48 (1H, s), 7.45-7.61 (6H, m), 7.64-7.70 (1H, m), 7.85 (2H, t, J=4.0 Hz)

ESI-MS (m/e): 439 [M+H]$^+$

Compounds of Examples 2 to 40 were obtained in the same manner as in Example 1, except for that the 4-(trifluoromethyl)phenyl isocyanate and the 3-phenylsulfonyl-8-azabicyclo[3.2.1]octane hydrochloride used in Example 1 were replaced with phenyl isocyanate and amine that are raw materials for the desired compounds.

Example 2

3-(4-fluorophenyl)sulfonyl-N-[(4-trifluoromethyl)phenyl]-8-azabicyclo[3.2.1]octane-8-carboxamide $^1$HNMR (400 MHz, CDCl$_3$, δppm): 1.96-2.06 (4H, m), 2.07-2.16 (2H, m), 2.40-2.51 (2H, m), 3.14-3.24 (1H, m), 4.33-4.39 (2H, m), 6.49 (1H, s), 7.22-7.28 (2H, m), 7.48 (2H, d, J=8.0 Hz), 7.53 (2H, d, J=8.0 Hz), 7.84-7.90 (2H, m)

ESI-MS (m/e): 457 [M+H]$^+$

Example 3

3-[(2-methoxyphenyl)sulfonyl]-N-[(4-trifluoromethyl)phenyl]-8-azabicyclo[3.2.1]octane-8-carboxamide $^1$HNMR (400 MHz, CDCl$_3$, δppm): 1.95-2.15 (6H, m), 2.39-2.51 (2H, m), 3.76-3.85 (1H, m), 3.88 (3H, s), 4.29-4.38 (2H, m), 6.61 (1H, s), 7.00 (1H, d, J=8.0 Hz), 7.12 (1H, t, J=8.0 Hz), 7.51-7.63 (5H, m), 7.96 (1H, d, J=8.0 Hz)

ESI-MS (m/e): 469 [M+H]$^+$

Example 4

3-[(3-methoxyphenyl)sulfonyl]-N-[(4-trifluoromethyl)phenyl]-8-azabicyclo[3.2.1]octane-8-carboxamide $^1$HNMR (400 MHz, CDCl$_3$, δppm): 1.97-2.14 (6H, m), 2.40-2.51 (2H, m), 3.19-3.28 (1H, m), 3.86 (3H, s), 4.32-4.39 (2H, m), 6.50 (1H, s), 7.17 (1H, d, J=8.0 Hz), 7.34 (1H, s), 7.40-7.55 (6H, m)

ESI-MS (m/e): 469 [M+H]$^+$

Example 5

3-[(4-methoxypheny)sulfonyl]-N-[(4-trifluoromethyl)phenyl]-8-azabicyclo[3.2.1]octane-8-carboxamide $^1$HNMR (400 MHz, CDCl$_3$, δppm): 1.93-2.14 (6H, m), 2.40-2.50 (2H, m), 3.11-3.22 (1H, m), 3.89 (3H, s), 4.31-4.39 (2H, m), 6.50 (1H, s), 7.01 (2H, d, J=8.0 Hz), 7.44-7.56 (4H, m), 7.78 (2H, d, J=8.0 Hz)

ESI-MS (m/e): 469 [M+H]$^+$

Example 6

3-[(2-chlorophenyl)sulfonyl]-N-[(4-trifluoromethyl)phenyl]-8-azabicyclo[3.2.1]octane-8-carboxamide $^1$HNMR (400 MHz, CDCl$_3$, δppm): 2.00-2.14 (6H, m), 2.42-2.53 (2H, m), 3.82-3.91 (1H, m), 4.33-4.39 (2H, m), 6.55 (1H, s), 7.46-7.62 (7H, m), 8.13 (1H, d, J=8.0 Hz)

ESI-MS (m/e): 473 [M+H]$^+$

Example 7

3-[(3-chlorophenyl)sulfonyl]-N-[(4-trifluoromethyl)phenyl]-8-azabicyclo[3.2.1]octane-8-carboxamide $^1$HNMR (400 MHz, CDCl$_3$, δppm): 1.96-2.06 (4H, m), 2.07-2.14 (2H, m), 3.18-3.17 (2H, m), 3.36-3.43 (1H, m), 4.34-4.40 (2H, m), 6.58 (1H, s), 7.45-7.55 (5H, m), 7.62-7.66 (1H, m) 7.72-7.76 (1H, m), 7.84-7.86 (1H, m)

ESI-MS (m/e): 473 [M+H]$^+$

Example 8

3-[(4-chlorophenyl)sulfonyl]-N-[(4-trifluoromethyl)phenyl]-8-azabicyclo[3.2.1]octane-8-carboxamide $^1$HNMR (400 MHz, CDCl$_3$, δppm): 1.93-2.03 (4H, m), 2.06-2.14 (2H, m), 2.40-2.49 (2H, m), 3.35-3.42 (1H, m), 4.33-4.40 (2H, m), 6.61 (1H, s), 7.46-7.58 (6H, m), 7.77-7.81 (2H, m)

ESI-MS (m/e): 473 [M+H]$^+$

Example 9

3-(pyridin-2-ylsulfonyl)-N-[(4-trifluoromethyl)phenyl]-8-azabicyclo[3.2.1]octane-8-carboxamide $^1$HNMR (400 MHz, CDCl$_3$, δppm): 2.08-2.17 (6H, m), 2.43-2.52 (2H, m), 3.05-3.14 (2H, m), 4.02-4.09 (1H, m), 6.54 (1H, s), 7.50-7.59 (5H, m), 7.99 (1H, t, J=8.0 Hz), 8.13 (1H, d, J=8.0 Hz), 8.71-8.75 (1H, d, m)

ESI-MS (m/e): 440 [M+H]$^+$

Example 10

3-(pyridin-3-ylsulfonyl)-N-[(4-trifluoromethyl)phenyl]-8-azabicyclo[3.2.1]octane-8-carboxamide $^1$HNMR (400 MHz, CDCl$_3$, δppm): 1.94-2.21 (6H, m), 2.38-2.52 (2H, m), 3.15-3.29 (1H, m), 4.34-4.45 (2H, m), 6.58 (1H, s), 7.43-7.61 (5H, m), 8.11-8.19 (1H, m), 8.87-8.95 (1H, m), 9.08 (1H, s)

ESI-MS (m/e): 440 [M+H]$^+$

Example 11

3-(pyridin-4-ylsulfonyl)-N-[(4-trifluoromethyl)phenyl]-8-azabicyclo[3.2.1]octane-8-carboxamide $^1$HNMR (400 MHz, CDCl$_3$, δppm): 1.97-2.06 (4H, m), 2.09-2.15 (2H, m), 2.40-3.53 (2H, m), 3.22-3.31 (1H, m), 4.35-4.41 (2H, m), 6.59 (1H, s), 7.45-7.56 (4H, m), 7.73 (2H, d, J=4.0 Hz), 8.92 (2H, d, J=4.0 Hz)

ESI-MS (m/e): 440 [M+H]$^+$

Example 12

3-(pyrimidin-2-ylsulfonyl)-N-[(4-trifluoromethyl)phenyl]-8-azabicyclo[3.2.1]octane-8-carboxamide ¹HNMR (400 MHz, CDCl₃, δppm): 2.08-2.24 (6H, m), 2.51-2.61 (2H, m), 4.16-4.25 (1H, m), 4.37-4.43 (2H, m), 6.70 (1H, s), 7.50-7.55 (4H, m), 7.56 (1H, t, J=4.0 Hz), 8.95 (2H, d, J=4.0 Hz)
ESI-MS (m/e): 441 [M+H]⁺

Example 13

N-phenyl-3-phenylsulfonyl-8-azabicyclo[3.2.1]octane-8-carboxamide

¹HNMR (400 MHz, CDCl₃, δppm): 1.93-2.01 (4H, m), 2.05-2.12 (2H, m), 2.39-2.50 (2H, m), 3.18-3.27 (1H, m), 4.30-4.36 (2H, m), 6.32 (1H, s), 7.03 (1H, t, J=4.0 Hz), 7.24-7.30 (2H, m), 7.32-7.37 (2H, m), 7.56 (2H, t, J=4.0 Hz), 7.66 (1H, t, J=4.0 Hz), 7.86 (2H, d, J=4.0 Hz)
ESI-MS (m/e): 371 [M+H]⁺

Example 14

N-(4-fluorophenyl)-3-phenylsulfonyl-8-azabicyclo[3.2.1]octane-8-carboxamide

¹HNMR (400 MHz, CDCl₃, δppm): 1.94-2.14 (6H, m), 2.39-2.50 (2H, m), 3.18-3.27 (1H, m), 4.28-4.37 (2H, m), 6.27 (1H, s), 6.97 (2H, t, J=4.0 Hz), 7.25-7.32 (2H, m), 7.57 (2H, t, J=8.0 Hz), 7.67 (1H, t, J=4.0 Hz), 7.86 (2H, d, J=4.0 Hz)

Example 15

N-(4-methylphenyl)-3-phenylsulfonyl-8-azabicyclo[3.2.1]octane-8-carboxamide

¹HNMR (400 MHz, CDCl₃, δppm): 1.89-2.11 (6H, m), 2.28 (3H, s), 2.39-2.48 (2H, m), 3.16-3.25 (1H, m), 4.29-4.36 (2H, m), 6.32 (1H, s), 7.07 (2H, d, J=8.0 Hz), 7.22 (2H, d, J=8.0 Hz), 7.56 (2H, t, J=8.0 Hz), 7.66 (1H, t, J=8.0 Hz), 7.86 (2H, d, J=8.0 Hz)
ESI-MS (m/e): 385 [M+H]⁺

Example 16

N-(4-isopropylphenyl)-3-phenylsulfonyl-8-azabicyclo[3.2.1]octane-8-carboxamide

¹HNMR (400 MHz, CDCl₃, δppm): 1.22 (6H, d, J=8.0 Hz), 1.92-2.00 (4H, m), 2.05-2.12 (2H, m), 2.40-2.49 (2H, m), 2.80-2.89 (1H, m), 3.16-3.25 (1H, m), 4.28-4.35 (2H, m), 6.29 (1H, s), 7.13 (2H, d, J=8.0 Hz), 7.25 (2H, d, J=8.0 Hz), 7.56 (2H, t, J=8.0 Hz), 7.66 (1H, t, J=8.0 Hz), 7.86 (2H, d, J=8.0 Hz)
ESI-MS (m/e): 413 [M+H]⁺

Example 17

N-(3-trifluoromethylphenyl)-3-phenylsulfonyl-8-azabicyclo[3.2.1]octane-8-carboxamide ¹HNMR (400 MHz, CDCl₃, δppm): 1.96-2.14 (6H, m), 2.40-2.50 (2H, m), 3.18-3.28 (1H, m), 4.33-4.39 (2H, m), 6.52 (1H, s), 7.26-7.30 (1H, m), 7.38 (1H, t, J=8.0 Hz), 7.53-7.60 (3H, m), 7.65-7.70 (2H, m), 7.86 (2H, d, J=8.0 Hz)
ESI-MS (m/e): 439 [M+H]⁺

Example 18

N-(2-trifluoromethylphenyl)-3-phenylsulfonyl-8-azabicyclo[3.2.1]octane-8-carboxamide ¹HNMR (400 MHz, CDCl₃, δppm): 1.98-2.07 (4H, m), 2.09-2.16 (2H, m), 2.39-2.48 (2H, m), 3.16-3.24 (1H, m), 4.28-4.35 (2H, m), 6.72 (1H, s), 7.15 (1H, t, J=8.0 Hz), 7.51 (1H, t, J=8.0 Hz), 7.56 (3H, t, J=8.0 Hz), 7.66 (1H, t, J=8.0 Hz), 7.86 (2H, d, J=8.0 Hz), 8.07 (1H, d, J=8.0 Hz)
ESI-MS (m/e): 439 [M+H]⁺

Example 19

N-(3,5-di-trifluoromethylphenyl)-3-phenylsulfonyl-8-azabicyclo[3.2.1]octane-8-carboxamide ¹HNMR (400 MHz, CDCl₃, δppm): 1.98-2.15 (6H, m), 2.39-2.49 (2H, m), 3.16-3.30 (1H, m), 4.33-4.42 (2H, m), 6.77 (1H, s), 7.21-7.26 (2H, t, J=8.0 Hz), 7.58 (2H, t, J=8.0 Hz), 7.83-7.92 (4H, m),
ESI-MS (m/e): 507 [M+H]⁺

Example 20

N-(4-cyclohexylphenyl)-3-phenylsulfonyl-8-azabicyclo[3.2.1]octane-8-carboxamide

¹HNMR (400 MHz, CDCl₃, δppm): 1.19-1.41 (6H, m), 1.58-1.86 (6H, m), 1.92-2.13 (4H, m), 2.39-2.48 (3H, m), 3.17-3.24 (1H, m), 4.29-4.34 (2H, m), 6.28 (1H, s), 7.11 (2H, d, J=8.0 Hz), 7.24 (2H, d, J=8.0 Hz), 7.56 (2H, t, J=8.0 Hz), 7.66 (1H, t, J=8.0 Hz), 7.85 (2H, d, J=8.0 Hz)
ESI-MS (m/e): 453 [M+H]⁺

Example 21

N-(2-methoxyphenyl)-3-phenylsulfonyl-8-azabicyclo[3.2.1]octane-8-carboxamide

¹HNMR (400 MHz, CDCl₃, δppm): 1.93-2.02 (4H, m), 2.08-2.15 (2H, m), 2.42-2.52 (2H, m), 3.18-3.27 (1H, m), 3.87 (3H, s), 4.30-4.39 (2H, m), 6.85 (1H, d, J=8.0 Hz), 6.94 (2H, t, J=8.0 Hz), 7.04 (1H, s), 7.53-7.59 (2H, m), 7.63-7.68 (1H, m), 7.86 (2H, d, J=8.0 Hz), 8.11 (1H, d, J=8.0 Hz)
ESI-MS (m/e): 401 [M+H]⁺

Example 22

N-(3-methoxyphenyl)-3-phenylsulfonyl-8-azabicyclo[3.2.1]octane-8-carboxamide

¹HNMR (400 MHz, CDCl₃, δppm): 1.93-2.00 (4H, m), 2.05-2.11 (2H, m), 2.39-2.49 (2H, m), 3.16-3.25 (1H, m), 3.78 (3H, s), 4.30-4.37 (2H, m), 6.38 (1H, s), 6.59 (1H, dd, J=8.3, 2.0 Hz), 6.81 (1H, dd, J=8.0, 1.2 Hz), 7.12-7.18 (2H, m), 7.56 (2H, t, J=8.0 Hz), 7.66 (1H, t, J=8.0 Hz), 7.86 (2H, d, J=8.0 Hz)
ESI-MS (m/e): 401 [M+H]⁺

Example 23

N-(4-methoxyphenyl)-3-phenylsulfonyl-8-azabicyclo[3.2.1]octane-8-carboxamide $^1$HNMR (400 MHz, CDCl$_3$, δppm): 1.89-1.98 (4H, m), 2.03-2.11 (2H, m), 2.39-2.49 (2H, m), 3.16-3.26 (1H, m), 3.77 (3H, s), 4.28-4.35 (2H, m), 6.30 (1H, s), 6.82 (2H, d, J=8.3 Hz), 7.23 (2H, d, J=8.0 Hz), 7.56 (2H, t, J=8.0 Hz), 7.66 (1H, t, J=8.0 Hz), 7.86 (2H, d, J=8.0 Hz)
ESI-MS (m/e): 401 [M+H]$^+$

Example 24

N-(4-isopropoxyphenyl)-3-phenylsulfonyl-8-azabicyclo[3.2.1]octane-8-carboxamide $^1$HNMR (400 MHz, CDCl$_3$, δppm): 1.30 (6H, d, J=4.0 Hz), 1.89-1.98 (4H, m), 2.03-2.11 (2H, m), 2.39-2.49 (2H, m), 3.16-3.26 (1H, m), 3.77 (3H, s), 4.28-4.35 (2H, m), 4.42-4.50 (1H, m), 6.22 (1H, s), 6.82 (2H, d, J=8.3 Hz), 7.21 (2H, d, J=8.0 Hz), 7.56 (2H, t, J=8.0 Hz), 7.66 (1H, t, J=8.0 Hz), 7.86 (2H, t, J=8.0 Hz)
ESI-MS (m/e): 429 [M+H]$^+$

Example 25

3-phenylsulfonyl-N-(pyridin-2-yl)-8-azabicyclo[3.2.1]octane-8-carboxamide $^1$HNMR (400 MHz, CDCl$_3$, δppm): 1.96-2.12 (6H, m), 2.38-2.47 (2H, m), 3.17-3.26 (1H, m), 4.36-4.42 (2H, m), 6.92-6.97 (1H, m), 7.18-7.25 (1H, m), 7.53-7.59 (2H, m), 7.61-7.69 (2H, m), 7.86 (2H, d, J=8.0 Hz), 8.02 (1H, d, J=8.0 Hz), 8.17 (1H, d, J=4.0 Hz)
ESI-MS (m/e): 372 [M+H]$^+$

Example 26

3-phenylsulfonyl-N-(pyridin-3-yl)-8-azabicyclo[3.2.1]octane-8-carboxamide $^1$HNMR (400 MHz, CDCl$_3$, δppm): 1.93-2.13 (6H, m), 2.37-2.48 (2H, m), 3.17-3.27 (1H, m), 4.36-4.43 (2H, m), 6.83 (1H, s), 7.20-7.25 (1H, m), 7.57 (2H, t, J=8.0 Hz), 7.61 (1H, t, J=8.0 Hz), 7.86 (2H, d, J=8.0 Hz), 8.02 (1H, d, J=8.0 Hz), 8.24 (1H, d, J=4.0 Hz), 8.47 (1H, s)
ESI-MS (m/e): 372 [M+H]$^+$

Example 27

3-phenylsulfonyl-N-(pyridin-4-yl)-8-azabicyclo[3.2.1]octane-8-carboxamide $^1$HNMR (400 MHz, CDCl$_3$, δppm): 1.94-2.12 (6H, m), 2.36-2.46 (2H, m), 3.16-3.25 (1H, m), 4.38-4.43 (2H, m), 7.19 (1H, s), 7.38 (2H, t, J=8.0 Hz), 7.57 (2H, t, J=8.0 Hz), 7.67 (1H, t, J=8.0 Hz), 7.85 (2H, d, J=8.0 Hz), 8.37 (2H, d, J=8.0 Hz)
ESI-MS (m/e): 372 [M+H]$^+$

Example 28

N-(4-chlorophenyl)-3-phenylsulfonyl-8-azabicyclo[3.2.1]octane-8-carboxamide $^1$HNMR (400 MHz, CDCl$_3$, δppm): 1.94-2.12 (6H, m), 2.38-2.49 (2H, m), 3.17-3.26 (1H, s), 4.29-4.36 (2H, m), 6.33 (1H, s), 7.23 (2H, d, J=8.0 Hz), 7.30 (2H, d, J=8.0 Hz), 7.57 (2H, t, J=8.0 Hz), 7.63-7.70 (1H, m), 7.86 (2H, d, J=8.0 Hz)
ESI-MS (m/e): 405 [M+H]$^+$

Example 29

N-biphenyl-4-yl-3-phenylsulfonyl-8-azabicyclo[3.2.1]octane-8-carboxamide $^1$HNMR (400 MHz, CDCl$_3$, δppm): 1.95-2.04 (2H, m), 2.08-2.16 (2H, m), 2.42-2.52 (2H, m), 3.06-3.16 (2H, m), 3.19-3.29 (1H, m), 4.34-4.42 (2H, m), 6.41 (1H, s), 7.38-7.45 (5H, m), 7.50-7.60 (7H, m), 7.84-7.89 (2H, m)
ESI-MS (m/e): 447 [M+H]$^+$

Example 30

3-phenylsulfonyl-N-[4-(1H-pyrazol-3-yl)phenyl]-8-azabicyclo[3.2.1]octane-8-carboxamide $^1$HNMR (400 MHz, CDCl$_3$, δppm): 1.92-2.12 (6H, m), 2.38-2.49 (2H, m), 3.17-3.27 (1H, m), 4.32-4.40 (2H, m), 6.54 (1H, s), 6.61 (1H, s), 7.39 (2H, d, J=8.0 Hz), 7.52-7.68 (7H, m), 7.85 (2H, d, J=8.0 Hz)
ESI-MS (m/e): 437 [M+H]$^+$

Example 31

3-phenylsulfonyl-N-[4-(1,3,4-thiadiazol-2-yl)phenyl]-8-azabicyclo[3.2.1]octane-8-carboxamide $^1$HNMR (400 MHz, CDCl$_3$, δppm): 1.98-2.15 (6H, m), 2.41-2.52 (2H, m), 3.21-3.30 (1H, m), 4.34-4.41 (2H, m), 6.55 (1H, s), 7.49-7.61 (4H, m), 7.64-7.71 (1H, m), 7.85-7.94 (4H, m), 9.06 (1H, s)
ESI-MS (m/e): 455 [M+H]$^+$

Example 32

3-phenylsulfonyl-N-[6-(trifluoromethyl)pyridin-3-yl]-8-azabicyclo[3.2.1]octane-8-carboxamide $^1$HNMR (400 MHz, CDCl$_3$, δppm): 2.01-2.14 (6H, m), 2.37-2.48 (2H, m), 3.19-3.27 (1H, m), 4.37-4.45 (2H, m), 7.07 (1H, s), 7.31-7.38 (1H, m), 7.54-7.63 (2H, m), 7.64-7.71 (1H, m), 7.82-7.93 (2H, m), 8.16 (1H, d, J=8.0 Hz), 8.44 (1H, s)
ESI-MS (m/e): 440 [M+H]$^+$

Example 33

3-phenylsulfonyl-N-[5-(trifluoromethyl)pyridin-3-yl]-8-azabicyclo[3.2.1]octane-8-carboxamide $^1$HNMR (400 MHz, CDCl$_3$, δppm): 1.99-2.17 (6H, m), 2.37-2.49 (2H, m), 3.19-3.30 (1H, m), 4.36-4.45 (2H, m), 7.07 (1H, d, J=8.0 Hz), 7.31-7.36 (1H, m), 7.55-7.62 (2H, m), 7.65-7.70 (1H, m), 7.83-7.92 (2H, m), 8.16 (1H, d, J=8.0 Hz), 8.44 (1H, s)
ESI-MS (m/e): 440 [M+H]$^+$

Example 34

3-(pyridin-2-ylsulfonyl)-N-[5-(trifluoromethyl)pyridin-2-yl)]-8-azabicyclo[3.2.1]octane-8-carboxamide $^1$HNMR (400 MHz, CDCl$_3$, δppm): 2.07-2.18 (6H, m), 2.42-2.51 (2H, m), 4.03-4.11 (1H, m), 4.36-4.44 (2H, m), 6.78 (1H, s), 7.54-7.64 (2H, m), 7.99 (1H, t, J=8.0 Hz), 8.13 (1H, d, J=4.0 Hz), 8.26 (1H, d, J=8.0 Hz), 8.50 (1H, s), 8.73 (1H, d, J=4.0 Hz)
ESI-MS (m/e): 441 [M+H]$^+$ Example 35

3-(pyrimidin-2-ylsulfonyl)-N-[5-(trifluoromethyl) pyridin-2-yl)]-8-azabicyclo[3.2.1]octane-8-carboxamide $^1$HNMR (400 MHz, CDCl$_3$, δppm): 2.08-2.30 (6H, m), 2.51-2.60 (2H, m), 4.19-4.27 (1H, m), 4.38-4.47 (2H, m), 6.71 (1H, s), 7.57-7.66 (2H, m), 8.28 (1H, dd, J=4.0, 8.0 Hz), 8.52 (1H, d, J=4.0 Hz), 8.96 (2H, d, J=4.0 Hz)
ESI-MS (m/e): 442 [M+H]$^+$ Example 36

N-(4-isopropylphenyl)-3-(pyridin-2-ylsulfonyl)-8-azabicyclo[3.2.1]octane-8-carboxamide $^1$HNMR (400 MHz, CDCl$_3$, δppm): 1.22 (6H, d, J=8.0 Hz), 2.02-2.12 (6H, m), 2.42-2.52 (2H, m), 2.81-2.90 (1H, m), 3.97-4.06 (1H, m), 4.30-4.35 (2H, m), 6.27 (1H, s), 7.14 (2H, d, J=8.0 Hz), 7.27 (2H, d, J=8.0 Hz), 7.53-7.58 (1H, m), 7.94-8.00 (1H, m), 8.12 (1H, d, J=8.0 Hz), 8.73 (1H, d, J=4.0 Hz)
ESI-MS (m/e): 414 [M+H]$^+$ Example 37

N-(4-isopropylphenyl)-3-(pyrimidin-2-ylsulfonyl)-8-azabicyclo[3.2.1]octane-8-carboxamide $^1$HNMR (400 MHz, CDCl$_3$, δppm): 1.22 (6H, d, J=8.0 Hz), 2.07-2.19 (6H, m), 2.50-2.60 (2H, m), 2.82-2.91 (1H, m), 4.15-4.23 (1H, m), 4.30-4.38 (2H, m), 6.30 (1H, s), 7.15 (2H, d, J=8.0 Hz), 7.29 (2H, d, J=8.0 Hz), 7.57 (1H, d, J=4.0 Hz), 8.95 (2H, d, J=4.0 Hz)
ESI-MS (m/e): 415 [M+H]$^+$ Example 38

3-(4H-1,2,4-triazol-3-ylsulfonyl)-N-[4-(trifluoromethyl)phenyl]-8-azabicyclo[3.2.1]octane-8-carboxamide $^1$HNMR (400 MHz, CD$_3$OD, δppm): 1.99-2.15 (6H, m), 2.40-2.54 (2H, m), 3.68-3.79 (1H, m), 4.45-4.54 (2H, m), 7.48-7.65 (4H, m), 8.66 (1H, s)
ESI-MS (m/e): 430 [M+H]$^+$ Example 39

3-(1,3-thiazol-2-ylsulfonyl)-N-[4-(trifluoromethyl)phenyl]-8-azabicyclo[3.2.1]octane-8-carboxamide $^1$HNMR (400 MHz, CDCl$_3$, δppm): 2.05-2.17 (4H, m), 2.18-2.26 (2H, m), 2.49-2.60 (2H, m), 3.82-3.90 (1H, m), 4.35-4.42 (2H, m), 6.52 (1H, s), 6.94 (2H, t, J=8.0 Hz), 7.04 (1H, s), 7.52 (1H, dd, J=4.0 Hz, 8.0 Hz), 7.76 (1H, d, J=4.0 Hz), 8.05 (1H, d, J=4.0 Hz)
ESI-MS (m/e): 446 [M+H]$^+$ Example 40

N-(4-tert-butylphenyl)-3-(pyridin-2-ylsulfonyl)-8-azabicyclo[3.2.1]octane-8-carboxamide $^1$HNMR (400 MHz, CDCl$_3$, δppm): 1.29 (9H, s), 2.03-2.13 (6H, m), 2.42-2.54 (2H, m), 3.97-4.06 (1H, m), 4.30-4.35 (2H, m), 6.26 (1H, s), 7.26-7.33 (4H, m), 7.53-7.58 (1H, m), 7.94-8.00 (1H, t, J=4.0 Hz), 8.12 (1H, d, J=8.0 Hz), 8.74 (1H, d, J=4.0 Hz)
ESI-MS (m/e): 428 [M+H]$^+$ Example 41

Production of 3-(pyridin-2-ylsulfonyl)-N-[4-(trifluoromethyl)phenyl]-3,8-azabicyclo[3.2.1]octane-8-carboxamide (1) Production of 3-benzyl-N-[4-(trifluoromethyl)phenyl]-3,8-azabicyclo[3.2.1]octane-8-carboxamide To a chloroform (3 mL) solution of 3-benzyl-3,8-diazabicyclo[3.2.1]octane dihydrochloride (100 mg) were added phenyl[4-(trifluoromethyl)phenyl]carbamate (133 mg) and triethylamine (0.203 mL), and the mixture was stirred at 80° C. for 24 hours. The organic layer was washed with distilled water and then dried over magnesium sulfate. After filtration, the solvent was distilled off under reduced pressure. The concentrated residue was purified by silica gel flash chromatography to give the target compound (130 mg).

(2) Production of N-[4-(trifluoromethyl)phenyl]-3,8-azabicyclo[3.2.1]octane-8-carboxamide To a methanol solution (3 mL) of the compound synthesized in (1) above (130 mg) was added palladium hydroxide (50 mg), and hydrogen (4 atm pressure) was added thereto at room temperature for 24 hours. The reaction mixture was filtered through Celite, followed by washing with methanol. The filtrate was concentrated to give the target compound (100 mg).

(3) Production of the Title Compound

To a chloroform solution (1 mL) of the compound synthesized in (2) above (25 mg) were added triethylamine (58 μL) and pyridine-2-sulfonyl chloride (16.3 mg), and the mixture was stirred at room temperature for 24 hours. The reaction mixture was washed with distilled water, and the organic layer was dried over magnesium sulfate. After filtration, the filtrate was distilled off under reduced pressure. The concentrated residue was purified by silica gel flash chromatography to give the title compound (24.7 mg).

$^1$HNMR (400 MHz, CDCl$_3$, δppm): 1.98-2.09 (4H, m), 3.11-3.19 (2H, m), 3.68-3.76 (2H, m), 4.36-4.45 (2H, m), 6.56-6.65 (1H, m), 7.43-7.56 (5H, m), 7.87-7.95 (2H, m), 8.63-8.68 (1H, m)
ESI-MS (m/e): 441 [M+H]$^+$

Example 42

Production of 5-(pyridin-2-ylsulfonyl)-N-[4-(trifluoromethyl)phenyl]-2,5-diazabicyclo[2.2.2]octane-2-carboxamide (1) Production of tert-butyl 5-({[4-(trifluoromethyl)phenyl]amino}carbonyl)-2,5-diazabicyclo[2.2.2]octane-2-carboxylate From tert-butyl 2,5-diazabicyclo[2.2.2]octane-2-carboxylate, the target compound was obtained in the same manner as in Example 41, (1).

(2) Production of N-[4-(trifluoromethyl)phenyl]-2,5-diazabicyclo[2.2.2]octane-2-carboxylate hydrochloride To a chloroform solution (3 mL) of the compound synthesized in (1) above (135 mg) was added a 4N hydrogen chloride-dioxane solution (3 mL), and the mixture was stirred at room temperature for 24 hours. The reaction mixture was concentrated under reduced pressure to give the target compound (107 mg).

(3) Production of the Title Compound

From the compound synthesized in (2) above, the title compound was obtained in the same manner as in Example 41, (3).

$^1$HNMR (400 MHz, CDCl$_3$, δppm): 1.77-1.89 (2H, m), 1.98-2.09 (1H, m), 2.13-2.23 (1H, m), 3.48-3.54 (1H, m), 3.59-3.65 (1H, m), 3.68-3.75 (1H, m), 3.98-4.06 (1H, m), 4.36-4.42 (1H, m), 4.52-4.60 (1H, m), 6.31-6.39 (1H, m), 7.42-7.56 (5H, m), 7.88-7.94 (1H, m), 7.97-8.02 (1H, m), 8.61-8.67 (1H, m)

ESI-MS (m/e): 441 [M+H]$^+$

INDUSTRIAL APPLICABILITY

The compound of the invention has excellent LCE inhibitory effect, and is useful as a remedy for various LCE-associated diseases, such as circulatory diseases, neurological diseases, metabolic diseases, reproductive system diseases, and digestive diseases, or as a herbicide.

The invention claimed is:

1. A compound represented by formula (I) or a pharmaceutically acceptable salt thereof:

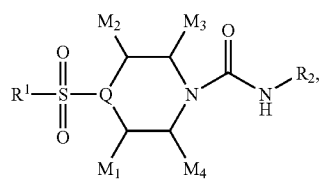

(I)

wherein:
R$^1$ represents unsubstituted or substituted C$_{1-6}$ alkyl, unsubstituted or substituted C$_{3-8}$ cycloalkyl, unsubstituted or substituted aryl, or unsubstituted or substituted heteroaryl, wherein the C$_{1-6}$ alkyl, C$_{3-8}$ cycloalkyl, aryl, or heteroaryl optionally having a substituent selected from the group consisting of halogen, C$_{1-6}$ alkyl, halo C$_{1-6}$ alkyl, C$_{1-6}$ alkyloxy, and halo C$_{1-6}$ alkyloxy;

R$^2$ represents unsubstituted or substituted phenyl or unsubstituted or substituted heteroaryl, wherein the phenyl or heteroaryl optionally having a substituent selected from the group consisting of halogen, C$_{1-6}$ alkyl, halo C$_{1-6}$ alkyl, C$_{3-8}$ cycloalkyl, C$_{1-6}$ alkyloxy, phenyl, and nitrogen-containing heteroaryl;

Q represents N or CH;

M$_1$ and M$_2$ each independently represent a hydrogen atom or C$_{1-6}$ alkyl optionally substituted with halogen; and M$_4$ forms, together with M$_2$ or M$_3$, —CH$_2$— or —CH$_2$—CH$_2$—, provided that M$_1$, M$_2$, M$_3$, and M$_4$ provide one —CH$_2$— or —CH$_2$—CH$_2$—.

2. A compound according to claim 1 or a pharmaceutically acceptable salt thereof, wherein R$^1$ is unsubstituted or substituted phenyl.

3. A compound according to claim 1 or a pharmaceutically acceptable salt thereof, wherein R$^1$ is unsubstituted or substituted pyridyl, unsubstituted or substituted pyrimidinyl, unsubstituted or substituted triazolyl, or unsubstituted or substituted thiazolyl.

4. A compound according to claim 1 or a pharmaceutically acceptable salt thereof, wherein R$^1$ is selected from the group consisting of phenyl, 4-fluorophenyl, 2-methoxypheny, 3-methoxypheny, 4-methoxypheny, 2-chlorophenyl, 3-chlorophenyl, 4-chlorophenyl, 2-pyrimidinyl, 2-pyridinyl, 3-pyridinyl, 4-pyridinyl, 1,2,4-triazol-3-yl, and thiazol-2-yl.

5. A compound according to claim 1 or a pharmaceutically acceptable salt thereof, wherein R$^2$ is unsubstituted or substituted phenyl or unsubstituted or substituted pyridinyl.

6. A compound according to claim 1 or a pharmaceutically acceptable salt thereof, wherein R$^2$ is selected from the group consisting of phenyl, 4-methylphenyl, 4-isopropylphenyl, 4-tert-butylphenyl, 4-fluorophenyl, 4-chlorophenyl, 4-trifluoromethylphenyl, 3-trifluoromethylphenyl, 2-trifluoromethylphenyl, 2-pyridinyl, 3-pyridinyl, 4-pyridinyl, 3,5-bis(trifluoromethyl)phenyl, 4-cyclohexylphenyl, 2-methoxypheny, 3-methoxypheny, 4-methoxypheny, 4-isopropyloxyphenyl, 4-biphenyl, 4-(1H-pyrazol-3-yl)-phenyl, 4-(1,3,4-thiadiazol-2-yl)-phenyl, 6-trifluoromethylpyridin-3-yl, and 5-trifluoromethylpyridin-2-yl.

7. A compound according to claim 1 or a pharmaceutically acceptable salt thereof, wherein M$_4$ forms, together with M$_3$, —CH$_2$— or —CH$_2$—CH$_2$—, and M$_1$ and M$_2$ are each independently a hydrogen atom or C$_{1-6}$ alkyl optionally substituted with halogen.

8. A compound according to claim 1 or a pharmaceutically acceptable salt thereof, wherein Q is CH.

9. A compound according to claim 1 or a pharmaceutically acceptable salt thereof, wherein Q is N.

10. A compound according to claim 1 or a pharmaceutically acceptable salt thereof, wherein the compound represented by formula (I) is selected from the group consisting of:
3-phenylsulfonyl-N-[(4-trifluoromethyl)phenyl]-8-azabicyclo[3.2.1]octane-8-carboxamide,
3-(4-fluorophenyl)sulfonyl-N-[(4-trifluoromethyl)phenyl]-8-azabicyclo[3.2.1]octane-8-carboxamide,
3-(pyridin-2-ylsulfonyl)-N-[(4-trifluoromethyl)phenyl]-8-azabicyclo[3.2.1]octane-8-carboxamide,
3-(pyrimidin-2-ylsulfonyl)-N-[(4-trifluoromethyl)phenyl]-8-azabicyclo[3.2.1]octane-8-carboxamide,
N-(4-isopropylphenyl)-3-phenylsulfonyl-8-azabicyclo[3.2.1]octane-8-carboxamide,
3-phenylsulfonyl-N-[6-(trifluoromethyl)pyridin-3-yl]-8-azabicyclo[3.2.1]octane-8-carboxamide, 3-phenylsulfonyl-N-[5-(trifluoromethyl)pyridin-3-yl]-8-azabicyclo[3.2.1]octane-8-carboxamide,
3-(pyrimidin-2-ylsulfonyl)-N-[5-(trifluoromethyl)pyridin-2-yl]]-8-azabicyclo[3.2.1]octane-8-carboxamide,
N-(4-isopropylphenyl)-3-(pyridin-2-ylsulfonyl)-8-azabicyclo[3.2.1]octane-8-carboxamide,
N-(4-isopropylphenyl)-3-(pyrimidin-2-ylsulfonyl)-8-azabicyclo[3.2.1]octane-8-carboxamide, and
N-(4-tert-butylphenyl)-3-(pyridin-2-ylsulfonyl)-8-azabicyclo[3.2.1]octane-8-carboxamide.

11. A pharmaceutical composition comprising a compound according to claim 1 or a pharmaceutically acceptable salt thereof.

* * * * *